United States Patent [19]

Schulze et al.

[11] 4,145,439

[45] Mar. 20, 1979

[54] COMBATING PESTS WITH BENZYL PHENYL ETHERS

[75] Inventors: Andreas Schulze, Cologne; Klaus Sasse, Berg.Gladbach; Klaus Naumann, Cologne; Peter Roessler, Berg.Gladbach; Peter Kraus, Cologne, all of Fed. Rep. of Germany

[73] Assignee: Bayer Aktiengesellschaft, Leverkusen, Fed. Rep. of Germany

[21] Appl. No.: 809,492

[22] Filed: Jun. 23, 1977

[30] Foreign Application Priority Data

Jul. 15, 1976 [DE] Fed. Rep. of Germany ....... 2631948

[51] Int. Cl.² .................. A01N 9/28; A01N 9/20; C07D 307/14; C07C 93/06
[52] U.S. Cl. ................... 424/285; 260/347.2; 260/347.7; 260/570.5 R; 260/570.5 P; 260/570.5 CA; 260/570.5 S; 260/570.7; 542/414; 424/330
[58] Field of Search .......... 260/347.7, 347.2, 570.5 R, 260/570.5 P, 570.5 CA, 570.5 S, 570.7; 542/414; 424/285, 330

[56] References Cited

U.S. PATENT DOCUMENTS 2,676,173   4/1954   Hiltmann et al. .................... 424/271

Primary Examiner—V. D. Turner
Attorney, Agent, or Firm—Sprung, Felfe, Horn, Lynch & Kramer

[57] ABSTRACT

Benzyl phenyl ethers, many of which are new, of the formula

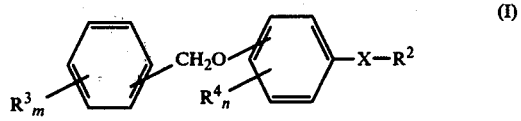

(I)

in which
X is

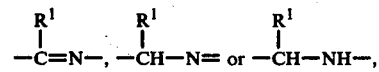

$R^1$ is H or alkyl,
$R^2$ is alkyl, alkenyl, alkynyl, alkylidene, alkenylidene or alkynylidene optionally substituted by OH, alkoxy, a heterocyclic group containing O, S or N, amino, monoalkylamino, dialkylamino or by an alkylene bridge with 5 carbon atoms,
$R^3$ each independently is H, alkyl, alkoxy, alkylmercapto, halogen, halogenoalkyl, halogenoalkoxy, halogenoalkylmercapto, $NO_2$, amino, monoalkylamino or dialkylamino,
$R^4$ each independently is H, halogen or alkoxy,
m is an integer from 1 to 5, and
n is an integer from 1 to 4,
and acid addition salts thereof, are useful for combatting arthropods, nematodes, fungi and bacteria.

8 Claims, No Drawings

COMBATING PESTS WITH BENZYL PHENYL ETHERS

The present invention relates to the use as pesticides of certain substituted benzyl phenyl ethers, some of which are known.

Pesticides are to be understood, in the present context, as agents which are suitable for combating animal pests as well as phytopathogenic fungi and bacteria.

It has already been disclosed to use synthetic juvenile hormones, such as isopropyl-(2 E, 4 E)-11-methoxy-3,7,11-trimethyl-2,4-dodecadienoate, for combating harmful insects. However, these compounds are obtainable only by means of involved and expensive syntheses. Furthermore, they are stable for only a short time when exposed to light and air. In addition, they are not suitable for combating insects that cause the greatest damage in the larva stage, since they only become effective when the imago develops from the larva stage.

It has further been disclosed in German Published Specification DOS 2,418,343 to use diphenyl ether derivatives for combatting harmful insects. However, the action of these compounds is not satisfactory, especially if low concentrations are used.

It has now been found that the substituted benzyl phenyl ethers of the general formula

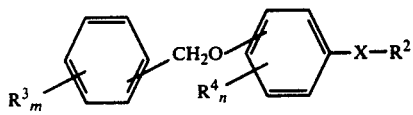

(I)

in which
X is

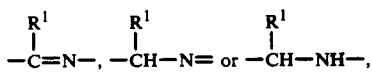

$R^1$ is H or alkyl,
$R^2$ is alkyl, alkenyl, alkynyl, alkylidene, alkenylidene or alkynylidene optionally substituted by OH, alkoxy, a heterocyclic group containing O, S or N, amino, monoalkylamino, dialkylamino or by an alkylene bridge with 5 carbon atoms,
$R^3$ each independently is H, alkyl, alkoxy, alkylmercapto, halogen, halogenoalkyl, halogenoalkoxy, halogenoalkylmercapto, $NO_2$, amino, monoalkylamino or dialkylamino,
$R^4$ each independently is H, halogen or alkoxy,
m is an integer from 1 to 5, and
n is an integer from 1 to 4,
and salts thereof exhibit powerful pesticidal, i.e. athropodicidal, nematicidal, fungicidal and bactericidal properties.

Salts with inorganic acids, such as HCl, HBr, HI, $H_2SO_4$, $H_3PO_4$, or with organic acids, such as formic acid, acetic acid, oxalic acid, sorbic acid or citric acid, are also suitable for use as pesticides.

Some of the active compounds of the general formula (I) are known from U.S. Pat. No. 2,676,173, German Offenlegungsschrift (German Published Specification) 2,364,191 and Tetrahedron Letters 1974 (26), 2261-4.

Some of the active compounds according to the invention are new and can, like the known compounds, be prepared by hydrogenating Schiff's bases of the general formula

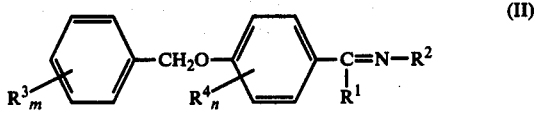

(II)

(III)

in which
$R^1$, $R^3$, $R^4$, m and n have the above-mentioned meanings and
$R^2$ is alkyl or alkylidene with 4-18 carbon atoms, alkenyl or alkenylidene with 3-8 carbon atoms or alkynyl or alkynylidene with 3-8 carbon atoms, each optionally substituted by an alkoxy radical with 1-6 carbon atoms as well as by OH, amino, monoalkylamino or dialkylamino with 1-6 carbon atoms in each alkyl moiety, an alkylene bridge with 5 carbon atoms, or furfuryl of the formula

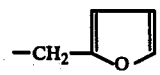

and if $R^3$ is not H, $R^2$ can, in addition to the above-mentioned meanings, be optionally substituted $C_{1-3}$ alkyl.

The new compounds are defined by the general formula

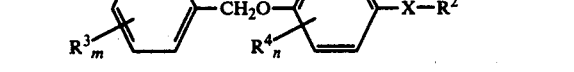

(IV)

in which
X, $R^2$, $R^3$, $R^4$, n and m have the meanings mentioned in connection with formulae (II) and (III).

The course of the reaction by which the new active compounds according to the invention are prepared can be illustrated by the following equation for the case of [4-(4-methylbenzyloxy)-benzylidene]-3-ethoxypropylamine and $NaBH_4$ serving as starting materials.

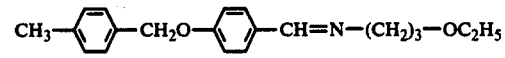

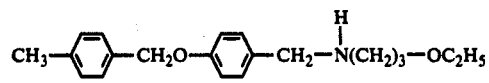

The hydrogenation can be carried out either with hydrogen under pressure in the presence of a suitable catalyst, such as Raney nickel, palladium or platinum, or with hydrogenating agents such as $NaBH_4$ or $LiAlH_4$, or with formic acid in the presence of a suitable diluent. In every case, the carbonyl compounds and amines from which the Schiff's bases of the formula (II) or (III) are formed can also be used as the starting materials directly, without intermediate isolation of the Schiff's bases.

The preparation of the active compounds of the formula (I) in which X represents the group

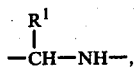

and of the new compounds of the formula (IV), can be carried out by catalytic hydrogenation of the corresponding Schiff's bases. Suitable diluents for the catalytic reduction of the Schiff's bases of the general formula (II) or (III) are all inert organic solvents, such as cyclohexane, benzine, benzene, toluene and xylene, and also alcohols, such as methanol, ethanol and isopropyl alcohol.

Examples of catalysts which can be used are Pd, Pt or Raney nickel.

The reaction temperatures can be varied within a fairly wide range. In general, the reaction is carried out at from 50° to 150° C., preferably at from 80° to 120° C.

The reaction is generally carried out at pressures of 60–150 bars, preferably of 80–120 bars.

Alternatively, the carbonyl compounds from which the Schiff's bases of the formula (II) or (III) are formed, together with the corresponding primary amines, can be reduced catalytically under the same conditions with hydrogen under pressure, while heating, to give the corresponding amines.

Hydrogenating agents which can be used are complex hydrides for example $LiAlH_4$, $NaBH_4$, $KBH_4$, $Na(OCH_3)_3BH$, $LiBH_4$ and $NaBH_4$, and $AlCl_3$. Suitable diluents for the hydrogenation with complex hydrides are all inert organic solvents, such as benzine, cyclohexane, toluene, xylene, or ethers such as diethyl ether, diisopropyl ether, 1,2-dimethoxyethane, dioxane or tetrahydrofuran, or mixtures of the stated solvents, for example ether/toluene. When using the less reactive hydrides such as, for example, $NaBH_4$, alcohols such as methanol, ethanol, propanol and isopropyl alcohol, $H_2O$, $NH_3$, amines such as methylamine, ethylamine, isopropylamine, ethylenediamine, aniline, pyridine and morpholine, acetonitrile, methylene chloride, chloroform or dimethylformamide can also be employed.

The reaction temperatures can be varied within a fairly wide range. In general, the reaction is carried out at from 0° C. to the boiling point of the solvent used, preferably from 20° to 70° C.

The reaction can be carried out under normal pressure or elevated pressure. It is advantageous to work under normal pressure.

In carrying out the process according to the invention, 0.25 to 1 mole of the complex hydride is employed per mole of the Schiff's base. Advantageously, an excess of reducing agent is used. When using $NaBH_4$ in ethanol, it is preferred to use from 0.4 to 0.7 mole of $NaBH_4$ per mole of the Schiff's base.

Both the active compounds of the formula (I) in which X represents the group

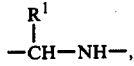

and the new compounds of the formula (IV), can be obtained by reduction of the corresponding Schiff's bases with formic acid.

The reaction can be carried out in the presence of a diluent; preferred diluents are inert organic solvents, for example hydrocarbons, such as benzene or toluene, and ethers such as diethyl ether.

The reducing agent used is 100% strength formic acid. The reaction temperatures can be varied within a fairly wide range. In general, the reaction is carried out at from 60° to 150°, preferably from 80° to the boiling point of the chosen solvent, up to 130° C. Usually, the reaction is carried out under normal pressure.

In carrying out the process according to the invention, it is preferred to use 2–5 moles of 100% strength formic acid per mole of Schiff's base.

In this reaction, again, it is alternatively possible directly to employ the amines and carbonyl compounds from which the Schiff's bases of the general formula (II) or (III) are formed.

Preferably, the Schiff's bases listed below are used for the preparation of the active compounds according to the invention:

(4-Benzyloxy-benzylidene)-1-methyl-propylamine, (4-benzyloxy-benzylidene)-n-hexylamine, (4-benzyloxy-benzylidene)-3-ethoxy-propylamine, (4-benzyloxy-benzylidene)-furfurylamine, (4-benzyloxy-benzylidene)-n-tetradecylamine, (4-benzyloxy-benzylidene)-n-hexadecylamine, (4-(4-methylbenzyloxy)-benzylidene)-1-methyl-propylamine, (4-(4-methyl-benzyloxy)-benzylidene)-n-hexylamine, (4-(4-methylbenzyloxy)-benzylidene)-2-ethyl-hexylamine, (4-(4-methylbenzyloxy)-benzylidene)-3-ethoxy-propylamine, (4-(4-methyl-benzyloxy)-benzylidene)-n-dodecylamine, (4-(4-methylbenzyloxy)-benzylidene)-n-tetradecylamine, (4-(4-methyl-benzyloxy)-benzylidene)-furfurylamine, (4-(3-methylbenzyloxy)-benzylidene)-1-methyl-propylamine, (4-(3-methylbenzyloxy)-benzylidene)-n-hexylamine, (4-(3-methyl-benzyloxy)-benzylidene)-2-ethyl-hexylamine, (4-(3-methyl-benzyloxy)-benzylidene)-3-ethoxy-propylamine, (4-(3-methyl-benzyloxy)-benzylidene)-n-dodecylamine, (4-(3-methyl-benzyloxy)-benzylidene)-n-tetradecylamine, (4-(3-methyl-benzyloxy)-benzylidene)-furfurylamine, (4-(4-ethyl-benzyloxy)-benzylidene)-1-methyl-propylamine, (4-(4-ethyl-benzyloxy)-benzylidene)-n-hexylamine, (4-(4-ethyl-benzyloxy)-benzylidene)-2-ethyl-hexylamine, (4-(4-ethyl-benzyloxy)-benzylidene)-3-ethoxy-propylamine, (4-(4-ethyl-benzyloxy)-benzylidene)-n-dodecylamine, (4-(4-ethyl-benzyloxy)-benzylidene)-n-tetradecylamine, (4-(4-ethyl-benzyloxy)-benzylidene)-furfurylamine, (4-(4-methoxy-benzyloxy)-benzylidene)-1-methyl-propylamine, (4-(4-methoxy-benzyloxy)-benzylidene)-n-hexylamine, (4-(4-methoxy-benzyloxy)-benzylidene)-2-ethylhexylamine, (4-(4-methoxy-benzyloxy)-benzylidene)-3-ethoxy-propylamine, (4-(4-methoxy-benzyloxy)-benzylidene)-n-dodecylamine, (4-(4-methoxy-benzyloxy)-benzylidene)-n-tetradecylamine, (4-(4-methoxy-benzyloxy)-benzylidene)-furfurylamine, (4-(4-ethoxy-benzyloxy)-benzylidene)-1-methyl-propylamine, (4-(4-ethoxy-benzyloxy)-benzylidene)-n-hexylamine, (4-(4-ethoxy-benzyloxy)-benzylidene)-2-ethylhexylamine, (4-(4-ethoxy-benzyloxy)-benzylidene)-3-ethoxypropylamine, (4-(4-ethoxy-benzyloxy)-benzylidene)-n-dodecylamine, (4-(4-ethoxy-benzyloxy)-benzylidene)-n-tetradecylamine, (4-(4-ethoxy-benzyloxy)-benzylidene)-furfurylamine, (4-(4-chloro-benzyloxy)-benzylidene)-1-methyl-propylamine, (4-(4-chloro-benzyloxy)-benzylidene)-n-hexylamine, (4-(4-chloro-benzyloxy)-benzylidene)-2-ethylhexylamine, (4-(4-chloro-benzyloxy)-benzylidene)-3-ethoxypropylamine, (4-(4-chloro-benzyloxy)-benzylidene)-n-dodecylamine, (4-(4-chloro-benzyloxy)-benzylidene)-n-tetradecylamine, (4-(4-chloro-benzyloxy)-benzylidene)-furfurylamine, (4-(3,4-dichloro-benzyloxy)-benzylidene)-1-methyl-propylamine, (4-(3,4-dichloro-benzyloxy)-benzylidene)-n-hexylamine, (4-(3,4-dichloro-benzyloxy)-benzylidene)-cyclohexylamine, (4-(3,4-dichloro-benzyloxy)-benzylidene)-2-ethylhexylamine, (4-(3,4-dichloro-benzyloxy)-benzylidene)-n-dodecylamine, (4-(3,4-dichloro-benzyloxy)-benzylidene)-n-tetradecylamine, (4-(3,4-dichloro-benzyloxy)-benzylidene)-3-ethoxy-propylamine, (4-(3,4-dichloro-benzyloxy)-benzylidene)-furfurylamine, (4-(3,4-dichloro-benzyloxy)-benzylidene)-hydroxy-ethylamine, (4-(3,4-dichloro-benzyloxy)-benzylidene)-n-heptylamine, (4-(4-fluoro-benzyloxy)-benzylidene)-1-methyl-propylamine, (4-(4-fluoro-benzyloxy)-benzylidene)-n-hexylamine, (4-(4-fluoro-benzyloxy)-benzylidene)-cyclohexylamine, (4-(4-fluoro-benzyloxy)-benzylidene)-2-ethylhexylamine, (4-(4-fluoro-benzyloxy)-benzylidene)-n-dodecylamine, (4-(4-fluoro-benzyloxy)-benzylidene)-n-tetradecylamine, (4-(4-fluoro-benzyloxy)-benzylidene)-3-ethoxy-propylamine, (4-(4-fluoro-benzyloxy)-benzylidene)-furfurylamine, (4-(4-fluoro-benzyloxy)-benzylidene)-2-hydroxy-ethylamine, (4-(4-fluoro-benzyloxy)-benzylidene)-n-heptylamine, (4-(3-fluoro-benzyloxy)-benzylidene)-1-methylpropylamine, (4-(3-fluoro-benzyloxy)-benzylidene)-n-hexylamine, (4-(3-fluoro-benzyloxy)-benzylidene)-cyclohexylamine, (4-(3-fluoro-benzyloxy)-benzylidene)-2-ethylhexylamine, (4-(3-fluoro-benzyloxy)-benzylidene)-n-dodecylamine, (4-(3-fluoro-benzyloxy)-benzylidene)-n-tetradecylamine, (4-(3- fluoro-benzyloxy)-benzylidene)-3-ethoxy-propylamine, (4-(3-fluoro-benzyloxy)-benzylidene)-furfurylamine, (4-(3-fluoro-benzyloxy)-benzylidene)-hydroxy-ethylamine, (4-(3-fluoro-benzyloxy)-benzylidene)-n-heptylamine, (4-(4-trifluoromethyl-benzyloxy)-benzylidene)-1-methyl-propylamine, (4-(4-trifluoromethyl-benzyloxy)-benzylidene)-n-hexylamine, (4-(4-trifluoromethyl-benzyloxy)-benzylidene)-cyclohexylamine, (4-(4-trifluoromethyl-benzyloxy)-benzylidene)-2-ethylhexylamine, (4-(4-trifluoromethyl-benzyloxy)-benzylidene)-n-dodecylamine, (4-(4-trifluoromethyl-benzyloxy)benzylidene)-n-tetradecylamine, (4-(4-trifluoromethylbenzyloxy)-benzylidene)-3-ethoxy-propylamine, (4-(4-trifluoromethyl-benzyloxy)-benzylidene)-furfurylamine, (4-(4-trifluoromethyl-benzyloxy)-benzylidene)-hydroxy-ethylamine, (4-(4-trifluoromethyl-benzyloxy)-benzylidene)-n-heptylamine, (4-(4-trifluoromethoxy-benzyloxy)-benzylidene)-1-methyl-propylamine, (4-(4-trifluoromethoxy-benzyloxy)-benzylidene)-n-hexylamine, (4-(4-trifluoromethoxy-benzyloxy)-benzylidene)-2-ethyl-hexylamine, (4-(4-trifluoromethoxy-benzyloxy)-benzylidene)-n-dodecylamine, (4-(4-trifluoromethoxy-benzyloxy)-benzylidene)-n-tetradecylamine, (4-(4-trifluoromethoxy-benzyloxy)-benzylidene)-3-ethoxypropylamine, (4-(4-trifluoromethoxy-benzyloxy)-benzylidene)-furfurylamine, (4-(4-trifluoromethoxy-benzyloxy)-benzylidene)-2-hydroxy-ethylamine, (4-(4-trifluoromethoxybenzyloxy)-benzylidene)-n-heptylamine, (4-(4-trifluoromethylthio-benzyloxy)-benzylidene)-1-methylpropylamine, (4-(4-trifluoromethylthio-benzyloxy)-benzylidene)-n-hexylamine, (4-(4-trifluoromethylthio-benzyloxy)-benzylidene)-cyclohexylamine, (4-(4-trifluoromethylthio-benzyloxy)benzylidene)-2-ethylhexylamine, (4-(4-trifluoromethylthio-benzyloxy)benzylidene)-n-dodecylamine, (4-(4-trifluoromethylthio-benzyloxy)-benzylidene)-n-tetradecylamine, (4-(4-trifluoromethylthio-benzyloxy)-benzylidene)-3-ethoxy-propylamine, (4-(4-trifluoromethylthio-benzyloxy)benzylidene)-furfurylamine, (4-(4-trifluoromethyl-thio-benzyloxy)benzylidene)-2-hydroxy-ethylamine, (4-(4-trifluoromethylthio-benzyloxy)benzylidene)-n-heptylamine, (4-(4-trifluoromethoxy-3-chloro-benzyloxy)-benzylidene)-1-methyl-propylamine, (4-(4-trifluoromethoxy-3-chloro-benzyloxy)-benzylidene)-n-hexylamine, (4-(4-trifluoromethoxy-3-chloro-benzyloxy)-benzylidene)-cyclohexylamine, (4-(4-trifluoromethoxy-3-chloro-benzyloxy)-benzylidene)-2-ethylhexylamine, (4-(4-trifluoromethoxy-3-chloro-benzyloxy)-benzylidene)-n-dodecylamine, (4-(4-trifluoromethoxy-3-chlorobenzyloxy)-benzylidene)-n-tetradecylamine, (4-(4-trifluoromethoxy-3-chloro-benzyloxy)-benzylidene)-3-ethoxy-propylamine, (4-(4-trifluoromethoxy-3-chlorobenzyloxy)-benzylidene)-furfurylamine, (4-(4-trifluoromethoxy-3-chlorobenzyloxy)-benzylidene)-2-hydroxy-ethylamine, (4-(4-trifluoromethoxy-3-chlorobenzyloxy)-benzylidene)-n-heptylamine, (4-(4-chloro-3-trifluoromethyl-benzyloxy)-benzylidene)-1-methyl-propylamine, (4-(4-chloro-3-trifluoromethyl-benzyloxy)-benzylidene)-n-hexylamine, (4-(4-chloro-3-trifluoromethyl-benzyloxy)-benzylidene)-cyclohexylamine, (4-(4-chloro-3-trifluoromethyl-benzyloxy)-benzylidene)-2-ethylhexylamine, (4-(4-chloro-3-trifluoromethyl-benzyloxy)-benzylidene)-n-dodecylamine, (4-(4-chloro-3-trifluoromethyl-benzyloxy)-benzylidene)-n-tetradecylamine, (4-(4-chloro-3-trifluoromethyl-benzyloxy)-benzylidene)-3-ethoxy-propylamine, (4-(4-chloro-3-trifluoromethyl-benzyloxy)-benzylidene)-furfurylamine, (4-(4-chloro-3-trifluoromethyl-benzyloxy)-benzylidene)-2-hydroxyethylamine, (4-(4-chloro-3-trifluoromethyl-benzyloxy)-benzylidene)-heptylamine, (4-(4-methyl-benzyloxy)-3,5-dibromo-benzylidene)-1-methyl-propylamine, (4-(4-methyl-benzyloxy)-3,5-dibromo-benzylidene)-n-hexylamine, (4-(4-methyl-benzyloxy)-3,5-dibromo-benzylidene)-cyclohexylamine, (4-(4-methyl-benzyloxy)-3,5-dibromo-benzylidene)-2-ethylhexylamine, 4-(4-methyl-benzyloxy)-3,5-dibromo-benzylidene)-n-dodecylamine, (4-(4-methyl-benzyloxy)-3,5-dibromo-benzylidene)-n-tetradecylamine, (4-(4-methyl-benzyloxy)-3,5-dibromo-benzylidene)-3-ethoxy-propylamine, (4-(4-methyl-benzyloxy)-3,5-dibromo-benzylidene)-furfurylamine, (4-(4-methyl-benzyloxy)-3,5-dibromo-benzylidene)-2-hydroxy-ethylamine, (4-(4-methyl-benzyloxy)-3,5-dibromo-benzylidene)-n-heptylamine, (4-(3,4-dichloro-benzyloxy)-3,5-dibromo-benzylidene)-1-methyl-propylamine, (4-(3,4-dichloro-benzyloxy)-3,5-dibromo-benzylidene)-n-hexylamine, (4-(3,4-dichloro-benzyloxy)-3,5-dibromo-benzylidene)-cyclohexylamine, (4-(3,4-dichloro-benzyloxy)-3,5-dibromo-benzylidene)-2-ethylhexylamine, (4-(3,4-dichloro-benzyloxy)-3,5-dibromo-benzylidene)-n-dodecylamine, (4-(3,4-dichloro-benzyloxy)-3,5-dibromo-benzylidene)-n-tetradecylamine, (4-(3,4-dichlorobenzyloxy)-3,5-dibromo-benzylidene)-3-ethoxy-propylamine, (4-(3,4-dichloro-benzyloxy)-3,5-dibromo-benzylidene)-furfurylamine, (4-(3,4-dichloro-benzyloxy)-3,5-dibromobenzylidene)-2-hydroxy-ethylamine, (4-( 3,4-dichlorobenzyloxy)-3,5-dibromo-benzylidene)-n-heptylamine, (4-(3,4-dimethyl-benzyloxy)-benzylidene-1-methylpropylamine, (4-(3,4-dimethyl-benzyloxy)-benzylidene-n-hexylamine, (4-(3,4-dimethyl-benzyloxy)-benzylidene-cyclohexylamine, (4-(3,4-dimethyl-benzyloxy)-benzylidene-2-ethylhexylamine, (4-(3,4-dimethyl-benzyloxy)-benzylidene-n-dodecylamine, (4-(3,4- dimethyl-benzyloxy)-benzylidene-n-tetradecylamine, (4-(3,4-dimethyl-benzyloxy)-benzylidene-3-ethyloxy-propylamine, (4-(3,4-dimethyl-benzyloxy)-benzylidene-furfurylamine, (4-(3,4-dimethyl-benzyloxy)-benzylidene-2-hydroxy-ethylamine, (4-(3,4-dimethyl-benzyloxy)-benzylidene-heptylamine, (4-(3,5-dimethylbenzyloxy)-benzylidene)-1-methyl-propylamine, (4-(3,5-dimethyl-benzyloxy)-benzylidene)-n-hexylamine, (4-(3,5-dimethyl-benzyloxy)-benzylidene)-cyclohexylamine, (4-(3,5-dimethyl-benzyloxy)-benzylidene)-2-ethylhexylamine, (4-(3,5-dimethyl-benzyloxy)-benzylidene)-n-dodecylamine, (4-(3,5-dimethyl-benzyloxy)-benzylidene)-n-tetradecylamine, (4-(3,5-dimethyl-benzyloxy)-benzylidene)-3-ethoxy-propylamine, (4-(3,5-dimethyl-benzyloxy)-benzylidene)-furfurylamine, (4-(3,5-dimethyl-benzyloxy)-benzylidene)-2-hydroxyethylamine, (4-(3,5-dimethyl-benzyloxy)-benzylidene)-heptylamine, (4-(trimethyl-benzyloxy)-benzylidene)-1-methyl-propylamine, (4-(trimethyl-benzyloxy)-benzylidene)-n-hexylamine, (4-(trimethyl-benzyloxy)-benzylidene)-cyclohexylamine, (4-(trimethyl-benzyloxy)-benzylidene)-2-ethylhexylamine, (4-(trimethyl-benzyloxy)-benzylidene)-n-dodecylamine, (4-(trimethyl-benzyloxy)-benzylidene)-n-tetradecylamine, (4-(trimethyl-benzyloxy)-benzylidene)-3-ethoxy-propylamine, (4-(trimethyl-benzyloxy)-benzylidene)-fufurylamine, (4-(trimethyl-benzyloxy)-benzylidene)-2-hydroxy-ethylamine, (4-(trimethyl-benzyloxy)-benzylidene)-heptylamine, (4-(4-nitro-benzyloxy)benzylidene)-1-methyl-propylamine, (4-(4-nitro-benzyloxy)-benzylidene)-n-hexylamine, (4-(4-nitro-benzyloxy)-benzylidene)-cyclohexylamine, (4-(4-nitro-benzyloxy)-benzylidene)-2-ethyl-hexylamine, (4-(4-nitro-benzyloxy)-benzylidene)-n-dodecylamine, (4-(4-nitro-benzyloxy)-benzylidene)-n-tetradecylamine, (4-(4-nitro-benzyloxy)-benzylidene)-3-ethoxy-propylamine, (4-(4-nitro-benzyloxy)-benzylidene)-furfurylamine, (4-(4-nitro-benzyloxy)-benzylidene)-2-hydroxy-ethylamine and (4-(4-nitro-benzyloxy)-benzylidene)-heptylamine.

The preparation of the active compounds of the formula (I), in which X represents the group

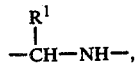

and of the new active compounds of the formula (IV), can also be carried out in accordance with the following processes (indicated only for the new active compounds), in which benzyl halides or tosylates of the general formula

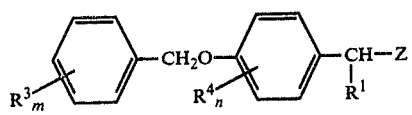

(V), in which

R$^1$, R$^3$, R$^4$, m and n have the above-mentioned meanings and

Z represents halogen or the tolylsulphonyl radical, are reacted with ammonia or an amine, or in which amides of the general formula

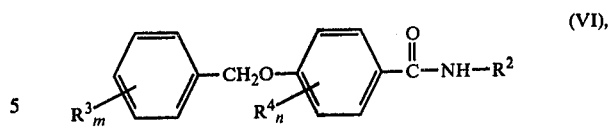

(VI), in which

R$^2$, R$^3$, R$^4$, m and n have the above-mentioned meanings, are reduced with hydrogen or a complex hydride. The latter process gives compounds of the general formula (I) or (IV) in which R$^1$ represents hydrogen.

Some of the Schiff's bases used for the preparation of the active compounds according to the invention are known. They can be prepared in accordance with methods which are in themselves known (see Houben-Weyl, Methoden der organischen Chemie (Methods of Organic Chemistry), Volume VII/1, year of publication 1954, pages 454–458, and Volume XI/2, year of publication 1958, pages 74–85).

The Schiff's bases of the formulae (II) and (III) are new. They are obtained by processes in which (a) carbonyl compounds of the general formula

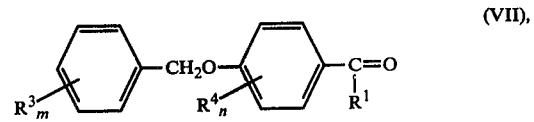

(VII), in which

R$^1$, R$^3$, R$^4$, n and m have the above-mentioned meanings, are reacted with amines of the general formula $$R^2 - NH_2 \quad \text{(VIII)},$$

in which

R$^2$ has the above-mentioned meaning, or in which (b) amines of the general formula

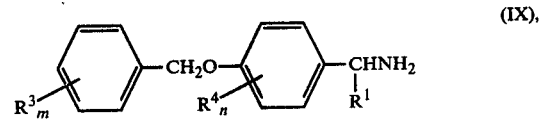

(IX), in which

R$^1$, R$^4$, R$^3$ m and n have the above-mentioned meanings, are reacted with carbonyl compounds of the general formula $$O = R^2 \quad \text{(X)},$$

in which

R$^2$ represents a doubly bonded radical having the above meaning.

These reactions can be carried out by heating the reactants without solvents, by heating in polar organic solvents such as alcohols or glacial acetic acid, or by heating in non-polar organic solvents such as toluene, xylene, cyclohexane and the like. These reactions can be catalysed by acids such as HCl or p-toluenesulphonic acid, by Lewis acids, such as ZnCl$_2$, or by alkalis. It is frequently advantageous to distil off azeotropically the water formed during the reaction.

The reaction can be carried out under normal pressure or elevated pressure.

The compounds of the general formulae (II) and (III) can also be prepared by alkylating a Schiff's base of the general formula (XI) with an alkylating agent of the general formula (XII) in the presence of a base. This process can be represented by the following general equation:

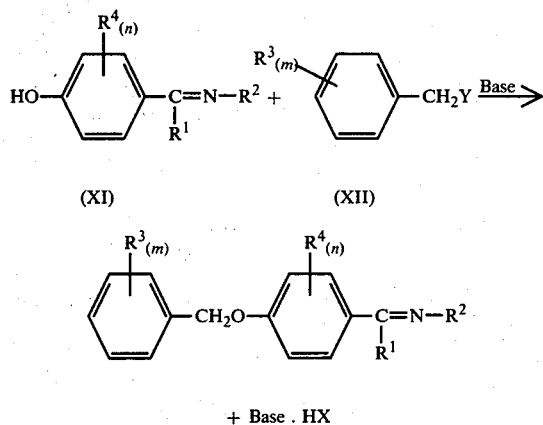

+ Base . HX in which
R¹, R², R³, R⁴, m and n have the above-mentioned meanings and
Y represents halogen (Cl, Br or I) or

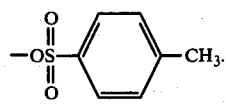

Most of the carbonyl compounds of the formulae (VII) and (X) used for the preparation of the Schiff's bases are known; new compounds can be prepared in accordance with known processes (see Journ. Org. Chem. (1951) page 16 and page 85 et seq.).

As already mentioned, the active compounds of the formula (I) are outstandingly suitable for combating pests. Amongst them, the new compounds of the formula (IV) are particularly suitable. Furthermore, those compounds of the formula (IV) are preferred, in which
X represents the radical

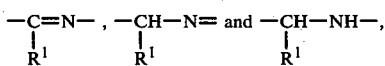

R² represents straight-chain, branched, or cyclic alkyl or alkylidene with 4-18 carbon atoms, propenyl, propargyl, or pentynyl, any of which can optionally be substituted by an alkoxy radical with 1-4 carbon atoms, OH, dimethylamino or diethylamino or by an alkylene bridge with 5 carbon atoms, or R² represents furfuryl, and, if R³ is not hydrogen, may also represent optionally substituted alkyl with 1-3 carbon atoms, R³ each independently represents hydrogen, alkyl with 1-4 carbon atoms, alkoxy with 1-4 carbon atoms (especially methoxy or ethoxy), halogen (especially chlorine and fluorine), trifluoromethyl, trichloromethyl, trifluoromethoxy, trifluoromethylmercapto or nitro, R⁴ each independently represents halogen (especially bromine or iodine), or alkoxy with 1-4 carbon atoms (especially methoxy).

Further particularly preferred compounds are those of the general formula (IV), in which
R¹ represents hydrogen, R² represents singly or doubly bonded alkyl with 4-14 carbon atoms which is optionally substituted by an alkoxy radical with 1-4 carbon atoms or by OH or dialkylamino with 1-4 carbon atoms per alkyl group, or represents propenyl, alkynyl with 3-8 carbon atoms, cycloalkyl with 5 or 6 carbon atoms or furfuryl.

The active compounds are well tolerated by plants, have a favorable level of toxicity to warm-blooded animals, and can be used for combating arthropod pests, especially insects and arachnids, and nematodes which are encountered in agriculture, in forestry, in the protection of stored products and of materials, and in the hygiene field. They are active against normally sensitive and resistant species and against all or some stages of development. The above-mentioned pests include:

from the class of the Isopoda, for example, *Oniscus asellus, Armadillidium vulgare* and *Porcellio scaber;* from the class of the Diplopoda, for example *Blaniulus guttulatus;* from the class of the Chilopoda, for example, *Geophilus carpophagus* and Scutigera spec.; from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.; from the order of the Anoplura, for example *Phylloxera vastatrix,* Pemphigus spp., *Pediculus humanus corporis,* Haematopinus spp. and Linognathus spp.; from the order of the Mallophaga, for example Trichodectes spp. and Damalinea spp.; from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.; from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.; from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus*

*surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.; from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.. from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp. and Trichodorus spp..

The active compounds according to the invention exhibit a powerful fungitoxic and bacteriotoxic action. They do not damage crop plants in the concentrations required for combating fungi and bacteria. For these reasons they are suitable for use as plant protection agents for combating fungi and bacteria. Fungitoxic agents in plant protection are employed for combating Plasmodiophoromycetes, Oomycetes, Chytridiomycetes, Zygomycetes, Ascomycetes, Basidiomycetes and Deuteromycetes.

The active compounds according to the invention have a broad spectrum of action and can be used against parasitic fungi which attack above-ground parts of plants or which attack the plants through the soil, as well as against seed-borne pathogens.

The active compounds according to the invention exhibit a particularly good activity against parasitic fungi which attack above-ground parts of plants, such as rust diseases on cereals, caused by species of Puccinia, and bean rust (*Uromyces phaseoli*), and also against powdery mildew, caused by species of Erysiphe, and powdery mildew of apples (*Podosphaera leucotricha*) and, in the case of rice, against *Pyricularia oryzae* and *Pellicularia sasakii.* On above-ground parts of plants, the compounds are also active against species of Botrytis, species of Septoria, and species of Cercospora. The active compounds according to the invention are effective, and of particular importance in practice, when they are employed as seed dressings or soil treatment agents against phytopathogenic fungi which adhere to the seed and occur in the soil, and in crop plants cause seedling diseases, root rots, tracheomycoses and seed diseases, such as species of Fusarium, species of Rhizoctonia, *Verticillium alboatrum* and *Phialophora cinerescens.*

The active compounds according to the invention can be combined with other active compounds to boost and supplement their spectrum of action, depending on the intended use. In particular, the active compounds mentioned below, and other representatives of the groups of active compounds characterized by those mentioned below, are suitable for this purpose.

Organic phosphorus compounds such as O,O-dimethyl-S-isopropyl-2-sulphinylethylthiophosphate, O,O-dimethyl-S-(2-methoxyethyl-acetamide)-dithiophosphate (Medithionat), O,O-diethyl-S-(N-ethoxycarbonyl-N-methylcarbamoyl-methyl)-dithiophosphate (Mecarbam), S-(5-methoxy-4-pyron-2-yl)-O,O-dimethylthiophosphate, O,S-dimethyl-N-acetyl-amido-thiophosphate (Acephate), 1-phenyl-3-(diethoxy-thiophosphoryloxy)-1,2,4-triazole (Triazophos), O,O-diethyl-O-[6-(3-(2-phenyl)-pyridazinonyl)]-thiophosphate, 4-dimethoxy-thiophosphoryloxy)-2-diethyl-amino-6-methyl-pyridimine (Pirimiphos-Methyl), 4-diethoxy-thiophosphoryloxy)-2-diethylamino-6-methyl-pyrimidine (Pirimiphos-Ethyl), O,O-diethyl-O-(3-chloro-7-methyl-2-pyrazolo-[1,5-α]-pyrimidinyl)-thiophosphate (Chloropyrophos), O-ethyl-S-n-propyl-O-(2,4-dichlorophenyl)-thiophosphate (Dichlorpropafos), O-ethyl-O-(4-methylmercaptophenyl)-S-n-propyldithiophosphate (Mercaptopropafos), O-ethyl-O-(2-carbisopropoxyphenyl)-isopropyl-amidothiophosphate (Isofenphos), S-chloromethyl-diethyl-phosphorothiolothionate (Chlormephos), S-(tert.-butylthio)-methyl-O,O-diethyl-dithiophosphate, O,O-diethyl-O-[0-chlorophenyl)-glyoxylonitrite-oxime]-thiophosphate (Chlorophoxim), O,O-diethyl-O-phenylglyoxylonitrile-oxime-thiophosphate (Methylphoxim), bis-O,O-diethyl-phosphoric acid anhydride (TEPP), dimethyl-(2,2,2-trichloro-1-hydroxyethyl)-phosphonate (Trichlorfon), 1,2-dibromo-2,2-dichloroethyl-dimethylphosphate (Naled), 2,2-dichlorovinyldimethylphosphate (Dichlorvos), 2-methoxycarbamyl-1-methylvinyldimethylphosphate (Mevinphos), dimethyl-1-methyl-2-(methylcarbamoyl)-vinylphosphate cis (Monocrotophos), 3-(dimethoxy-phosphinyloxy)-N,N-dimethyl-cis-crotonamide (Dicrotophos), 2-chloro-2-diethylcarbamoyl-1-methyl-vinyldimethylphosphate (Phosphamidon), O,O-diethyl-O-(or S)-2-(ethylthio)-ethylthiophosphate (Demeton), S-ethylthioethyl-O,O-dimethyl-dithiophosphate (Thiometon), O,O-diethyl-S-ethylmercaptomethyldithiophosphate (Phorate), O,O-diethyl-S-2-ethylthioethyl dithiophosphate (Disulfoton), O,O-dimethyl-S-2-(ethylsulphinyl)-ethylthiophosphate (Oxydemeton-methyl), O,O-dimethyl-S-(1,2-dicarbethoxyethyldithiophosphate (Malathion), O,O,O,O-tetraethyl-S,S'-methylene-bis-dithiophosphate (Ethion), O-ethyl-S,S-dipropyldithiophosphate (Prophos), O,O-dimethyl-S-(N-methyl-N-formylcarbamoylmethyl)-dithiophosphate (Formothion), O,O-dimethyl-S-(N-methylcarbamoylmethyl)-dithiophosphate (Dimethoat), O,O-dimethyl-O-p-nitrophenyl-thiophosphate (Parathion-methyl), O,O-diethyl-O-p-nitrophenyl-thiophosphate (Parathion), O-ethyl-O-p-nitrophenylphenylthiophosphonate (EPN), O,O-dimethyl-O-(4-nitro-m-tolyl)thiophosphate (Fenitrothion), O,O-dimethyl-O-2,4-5-trichlorophenyl-thiophosphate (Ronnel), O-ethyl-O-2,4,5-trichlorophenylethylthiophosphonate (Trichloronat), O,O-dimethyl-O-2,5-dichloro-4-bromophenylthiophosphate (Bromophos), O,O-dimethyl-O-(2,5-dichloro-4-iodophenyl)-thiophosphate (Iodofenphos), 4-tert.-butyl-2- chlorophenyl-N-methyl-O-methylamidophosphate (Crufomat), O,O-dimethyl-O-3-(3-methyl-4-methylmercaptophenyl)-thiophosphate (Fenthion), isopropylamino-O-ethyl-O-(4-methylmercapto-3-methylphenyl)-phosphate (Phenamiphos), O,O-diethyl-O-p-(methylsulphinyl)-phenyl-thiophosphate (Fensulfothion), O-p-(dimethylsulphamido)-phenyl-O,O-dimethylthiophosphate (Famphur), O,O,O',O'-tetramethyl-O,O'-thiodi-p-phenylenethiophosphate, O-ethyl-S-phenylethyldithiophosphate (Fonofos), O,O-dimethyl-O-(α-methylbenzyl-3-hydroxycrotonyl)-phosphate, 2-chloro-1-(2,4-dichlorophenyl)-vinyl-diethylphosphate (Chlorfenvinphos), 2-chloro-1-(2,4,5-trichlorophenyl)-vinyl-dimethylphosphate, O-[2-chloro-1-(2,5-dichlorophenyl)]-vinyl-O,O-diethylthiophosphate, phenylglyoxylonitrile-oxime-O,O-diethylthiophosphate (Phoxim), O,O-diethyl-O-(3-chloro-4-methyl-2-oxo-2-H-1-benzopyran-7-yl)-thiophosphate (Coumaphos), 2,3-p-dioxanedithiol-S,S-bis-(O,O-diethyldithiophosphate) (Dioxathion), 5-[(6-chloro-2-oxo-3-benzoxazolinyl)-methyl]-O,O-diethyldithiophosphate (Phosalon), 2-(diethoxy-phosphinylimino)-1,3-dithiolane (Phosfolan), O,O-dimethyl-S-[2-methoxy-1,3,4-thiadiazol-5-(4H)-onyl-(4)-methyl]-dithiophosphate (Methidathion), O,O-dimethyl-S-phthalimidomethyldithiophosphate (Imidan), O,O-diethyl-O-(3,5,6-trichloro-2-pyridyl)-thiophosphate (Chloropyrifos), O,O-diethyl-O-2-pyrazinyl-thiophosphate (Thionazin), O,O-diethyl-O-(2-isopropyl-4-methyl-6-pyrimidyl)-thiophosphate (Diazinon), O,O-diethyl-O-(2-quinoxalyl)-thiophosphate (Quinalphos), O,O-dimethyl-S-(4-oxo-),2,3-benzotriazin-3-(4H)-yl-methyl)-dithiophosphate (Azinphosmethyl), O,O-diethyl-S-(4-oxo-1,2,3-benzotriazin-3-(4H)-ylmethyl-dithiophosphate (Azinphosethyl), S-[4,6-diamino-s-triazin-2-yl)-methyl]-O,O-dimethyldithiophosphate (Menazon), O,O-dimethyl-O-(3-chloro- 4-nitrophenyl)-thiophosphate (Chlorthion), O,O-dimethyl-O-(or S)-2-(ethylthioethyl)-thiophosphate (Demeton-S-methyl), 2-(O,O-dimethyl-phosphoryl-thiomethyl)-5-methoxy-pyrone-4,3,4-dichlorobenzyl-triphenylphosphonium chloride, O,O-diethyl-S-(2,5-dichlorophenylthiomethyl)-dithiophosphate (Phenkapton), 5-azino-bis-(dimethylamido)-phosphinyl-3-phenyl-1,2,4-triazole (Triamiphos), N-methyl-5-(O,O-dimethylthiolphosphoryl)-3-thiavaleramide (Vamidothion), O,O-dimethyl-S-(methylcarbamoylmethyl)-thiophosphate (Omethoat), O-ethyl-O-(8-quinolinyl)-phenylthiophosphonate (Oxinothiophos), O-methyl-S-methyl-amidothiophosphate (Methamidophos), O-methyl-O-(2,5-dichloro-4-bromophenyl)-benzothiophosphonate (Phosvel), O,O-diethyl-S-(N-isopropylcarbamoylmethyl)-dithiophosphate (Prothoat), S-N-(1-cyano-1-methylethyl)-carbamoyl-methyldiethyl-thiolphosphate (Cyanthoat), S-(2-acetamidoethyl)-O,O-dimethyl-dithiophosphate, O,O-dimethyl-O-(2-chloro-4-nitrophenyl)-thiophosphate (Dicapthon), O,O-dimethyl-O-p-cyanophenyl-thiophosphate (Cyanox), O-ethyl-O-p-cyanophenylthiophosphonate, O,O-diethyl-0,2,4-dichlorophenylthiophosphate (Dichlorfenthion), O,O-diethyl-O-2,5-dichloro-4-bromophenylthiophosphate (Bromophosethyl), dimethyl-p-(methylthio)-phenylphosphate, O,O-dimethyl-O-p-sulphamidophenylthiophosphate, O-[p-(p-chlorophenyl)-azophenyl]-O,O-dimethylthiophosphate (Azothoat), O,O-dimetyl-S-p-chlorophenyl-thiophosphate, O,O-dimethyl-S-(p-chlorophenylthiomethyl)-dithiophosphate (Methylcarbophenothion), O,O-diethyl-p-chlorophenyl-mercaptomethyl-dithiophosphate (Carbophenothion), O,O-diethyl-S-p-chlorophenylthiomethyl-thiophosphate, O,O-dimethyl-S-(carbethoxy-phenylmethyl)-dithiophosphate (Phenthoat), O,O-diethyl-7-hydroxy-3,4-tetramethylene-courmarinyl-thiophosphate (Coumithoat), 2-methoxy-4-H-1,3,2-benzodioxaphosphorine-2-sulphide, S-(2-chloro-1-phthalimidoethyl)-O,O-diethyldithiophosphate (Dialiflor), N-hydroxynaphthalimido-diethylphosphate, O,O-dimethyl-O-(3,5,6-trichloro-2-pyridyl)-thiophosphate, S-2-(ethylsulphonyl)-ethyl-dimethylthiolphosphate (Dioxydemeton-S-Methyl), diethyl-S-2-ethylsulphinyl)-ethyl-dithiophosphate (Oxydisulfoton), bis-O,O-diethylthiophosphoric acid anhydride (Sulfotep), dimethyl-1,3-di-(carbomethoxy)-1-propen-2-yl-phosphate, dimethyl-(2,2,2-trichloro-1-butyroxyloxyethyl)-phosphonate (Butonat), dimethyl-N-methoxymethylcarbamoylmethyldithiophosphate (Formocarbam), O-ethyl-S,S-diphenyldithiolphosphate (Ediphenphos), diisopropylaminofluophosphate (Mipafox), O,O-dimethyl-S-(morpholinylcarbamoylmethyl)-dithiophosphate (Morphothion), Octamethylpyrophosphoramide (Schradan), N,N,N',N'-tetramethyldiamidofluophosphate (Dimefox), O-methyl-O-(2-carbisopropoxyphenyl)-amidothiophosphate (Isocarbophos), as well as nitrophenols and their derivatives, such as the Na salt of 4,6-dinitro-6-methylphenol [dinitrocresol], the 2,2',2"-triehanolamine salt of dinitrobutylphenol, 2-(1-methylheptyl)-4,6-dinitrophenyl crotonate [Dinocap], 2-sec.-butyl-4,6-dinitrophenyl 3-methyl-butenoate [Binapacryl] and 2-sec.-butyl-4,6-dinitrophenyl isopropyl carbonate [Dinobuton] as well as dichlorodiphenyltrichloroethane (DDT), 2,2-bis-(p-chlorophenyl)-1,1-dichloroethane (TDE), bis-(p-chlorophenyl)-trichloroethanol (Dicofol), ethyl-4,4'-dichlorodiphenyl glycollate (Chlorobenzilate), isopropyl-4,4'-dichlorobenzilate (Chloropropylate), isopropyl-4,4'-dibromobenzilate (Phenisobromolate), 1,1,1-trichloro-2,2-bis-(p-methoxyphenyl)-ethane (Methoxychlor), 1,1-bis-(p-ethylphenyl)-2,2-dichloroethane (Perthane), bis-(4-chlorophenyl)-cyclopropylcarbinol (Kilacar), dichlorophenyl benzenesulphonate (Genite), 4-chlorpheny-2,4,5-trichlorophenyl-azo-sulphide (Milbex), 2-(p-tert.-butylphenoxy)-isopropyl 2'-chloroethyl sulphite (Aracide), 2-(p-tert.-butylphenoxy)-cyclohexyl-2-propinyl sulphite (Omite), 2-fluoro-N-methyl-N-1-naphthylacetamide (Nissol), N-dichlorofluoromethylthio-dimethylaminosulphonic acid anilide (Dichlofluanid), N-[(dichlorofluoromethyl)-thio]-N',N'-dimethyl-N-p-tolylsulphamide (Tolylfluanid), 1,2-dibromo-3-chloropropane (DBCP), 1,5-bis-(2,4-dimethylphenyl)-3-methyl-1,3,5-triazapenta-1,4-diene (Amitraz), ethyl-O-benzoyl-3-chloro-2,6-dimethoxybenzohydroximate (Benzomate), tricyclohexyltin hydroxide (Plictran), 1-tricyclohexylstannyl-1,2,4-triazole (Tricyclazol), torque (Neostanox), isopropyl 11-methoxy-3,7,11-trimethyldodeca-2,4-dienoate (Altosid), ethyl 3,7,11-trimethyl-2,4-dodecadienoate (Altozar), 2,2,2-trichloro-1-(3,4-dichlorophenyl)-ethanol acetate (Dichlorfenat), pyrethrin I, pyrethrin II, 3-allyl-2-methyl-4-oxo-2-cyclopenten-1-yl-chrysanthemumate (Allethrin), 6-chloriperonyl-chrysanthemumate (Barthrin), 2,4-dimethylbenzyl-chrysanthemumate ((Dimethrin), 2,3,4,5-tetrahydrophthalimido-methylchrysanthemumate, 6-methyl-2-oxo-1,3-dithiolo-[4,5-b]-quinoxalin (Quinomethionat), (1)-3-(2-furfuryl)-2-methyl-4-oxocyclopent-2-enyl(1)-(cis + trans) chrysanthemummonocarboxylate (Furethrin), 4-chlorobenzyl-4-fluorphenyl sulphide (Fluorbenside), 5,6-dichloro-1-phenoxycarbanyl-2-trifluoromethyl-benzimidazole (Fenozaflor), p-chlorophenyl p-chlorobenzene-sulphonate (Ovex), p-chlorophenyl-benzenesulphonate (Fenson), p-chlorophenyl-2,4,5-trichlorophenylsulphone (Tetradifon), p-chlorophenyl-2,4,5-trichlorophenyl-sulphide (Tetrasul), p-chlorobenzyl-p-chlorophenyl-sulphide (Chlorbenside), 2-thio-1,3-dithiolo(5,6)-quinoxaline (Thiochinox), prop-2-ynyl-(4-1-butylphenoxy)-cyclohexyl sulphite (Propargil), 1-dimethyl-2-(2'-methyl-4'-chlorophenyl)-formamidine (Chlorphenamidin) and also ureas such as 1-(2,6-dichlorobenzoyl)-3-(3,4-dichlorophenyl)-urea (DU 19,111), 1-(2,6-dichlorobenzoyl)-3-(4-chlorophenyl)-urea (pH 60-38), 1-(2,6-difluorobenzoyl)-3-(4-chlorophenyl)-urea (pH 60-40), N-2-methyl-4-chlorophenyl-N',N'-dimethyl-thiourea and carbamates such as 2-methylthio-O-(N-methyl-carbamoyl)-butan-3-one-oxime (Butocarboxim = Blumi), (2-ethylmercaptomethylphenyl)-N-methylcarbamate (Ethiophencarb), 1-dimethylcarbamoyl)-N-(methylcarbamoyloxy)-thioformhydroximic acid methyl ester (Oxamyl = Vydate), 2,2-dimethyl-1,3-benzodioxol-4-yl-N-methyl-carbamate (Bendoxicarb), 1-naphthyl-N-methylcarbamate (Carbaryl), 4-dimethylamino-3,5-xylyl-N-methylcarbamate, 4-dimethylamino-3-tolyl-N-methylcarbamate (Aminocarb), 4-methylthio-3,5-xylyl-N-methylcarbamate (Methiocarb), 3,4,5-trimethylphenyl-N-methylcarbamate, 2-chlorophenyl-N-methylcarbamate (CPMC), 5-chloro-6-oxo-2-norbornanecarbonitrile-O-(methylcarbamoyl)-oxime, 1-(dimethylcarbamoyl)-5-methyl-3-pyrazolyl)-N,N-dimethylcarbamate (Dimetilan), 2,3-dihydro-2,2-dimethyl-7-benzofuranyl-N-methylcarbamate(Carbofuran), 2-methyl-2-methylthiopropionaldehyde-O-(methylcarbamoyl)-oxime (Aldicarb), n-(1-ethylpropyl)-phenyl-N-methylcarbamate, 3,5-di-tert.-butyl-N-methylcarbmate, n-(1-methylbutyl)-phenyl-N-methylcarbamate, 2-isopropylphenyl-N-methylcarbamate (Isoprocarb), 2-sec.-butylphenyl-N-methylcarbamate, 3-isopropyl-5-methylphenyl-N-methylcarbamate (Promecarb), 2-(1,3-dioxolan-2-yl)-phenyl-N-methylcarbamate (Dioxacarb), 2-isopropoxyphenyl-N-methylcarbamate (Arprocarb), 4-diallylamino-3,5-xylyl-N-methylcarbamate (Allyxicarb), 2,3-dihydro-2-methyl-7-benzofuranyl-N-methylcarbamate (Decarbofuran), 1-isopropyl-3-methylpyrazol-5-yl-N,N-dimethylcarbamate (Isolan), 2-dimethylamino-5,6-dimethylpyrimidin-4-yl-N,N-dimethylcarbamate (Pirimicarb), 3,4-dimethylphenyl-N-methylcarbamate, 3-dimethylamino-methyleneiminophenyl-N-methylcarbamate (Formetanate) and its salts, 1-methylthioethyl-imino-N-methylcarbamate (Methomyl), 1,3-bis-(carbamoylthio)-2-(N,N-dimethylamino)-propane hydrochloride, 5,5-dimethylhydroresorcinoldimethylcarbamate and chlorinated hydrocarbons such as 6,7,8,9,10,10-hexachloro-1,5,5a,6,9,9a-hexahydro-6,9-methane-2,4,3-benzodioxathiepine-3-oxide (Endosulfan), chlorinated camphene containing 67–69% of chlorine (Toxaphen), chlorinated terpenes (Strobane), 1,2,3,5,6,7,8,9,10,10-decachloro-pentacyclo-[5.2.1.0$^{2.6}$.0$^{3.9}$.0$^{5.8}$]-decan-4-one (Chlordecone), dodecachlorooctahydro-1,3,4-metheno-2H-cyclobuta-(cd)-pentalene (Mirex), decachlorobi-2,4-cyclopentadien-1-yl (Dekaflor), ethyl 1,1a,3,3a,4,5,5,5a,5b,6-decachloroöctahydro-2-hydroxy-1,3,4-metheno-(2H)-cyclobuta-[cd]-pentalene-2-levulinate (Kelevan), γ-hexachlorocyclohexane (Gammexane; lindane; γ-HCH), 1,2,4,5,6,7,8,8-octachloro-3a,4,7,7a'-tetrahydro-4,7-methylene-indane (Chlordane), 1,4,5,6,7,8,8-heptachloro, 3a,4,7,7a-tetrahydro-4,7-methyleneindane (Heptachlor), 1,2,3,4,10,10-hexachloro-6,7-epoxy-1,4,4a,5,6,7,8,8a-octahydro-endo-endo-5,8-dimethanonaphthalene (Endrin) and also pheromones, synergistic agents, repellents, vegetable active compounds, metabolism products of micro-organisms and development inhibitors.

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons, e.g. dichlorodifluoromethane and trichlorofluoromethane, as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other arthropodicides, nematicides, fungicides and bactericides, or rodenticides, herbicides, fertilizers, growth-regulating agents, etc., as illustratively outlined hereinabove, if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. arthropods, nematodes, fungi and bacteria, which comprises applying to at least one of correspondingly (a) such arthropods, (b) such nematodes, (c) such fungi, (d) such bacteria, and (e) the corresponding habitat thereof, i.e. the locus to be protected, e.g. to a growing crop, to an area where a crop is to be grown or to a domestic animal, a correspondingly combative or toxic amount, i.e. an arthropodicidally, nematicidally, fungicidally or bactericidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated without limitation by the following experiments which show the insect growth regulation action, as well as the fungitoxic and bacteriotoxic action, of the compounds according to the invention; it is intended to imply a limitation in respect of the breadth of action of these compounds In the case of the experiments on the insect growth inhibition, the morphological changes, such as halfpupated animals, incompletely hatched larvae or caterpillars, defective wings or pupal cuticula in imagos, as well as the mortality, are assessed throughout the indicated development of the test insects. The sum of the morphological malformations and of the mortality during development is shown as a percentage of the number of test animals.

EXAMPLE 1

Growth-Inhibiting/Ingestion Test

Test insects: *Plutella maculipennis* (caterpillars in the 4th stage of development) — 20 specimens; *Phaedon cochleariae* (larvae in the 4th stage of development) — 20 specimens Feed plants: cabbage plants (*Brassica oleracea*)

Solvent: 10 parts by weight of acetone

Emulsifier: 1 part by weight of polyoxyethylene-(20)-sorbitan monolaurate

To produce a suitable preparation of active compound, 2 parts by weight of active compound were mixed with the stated amount of solvent and emulsifier and with sufficient water to give a 1% strength mixture, which was diluted with water to the desired concentration.

The test insects were fed with leaves of the feed plants, which were provided with the uniform spray coating of the active compound mixture of the chosen concentration, so that the stated active compound concentrations in ppm (parts per million) relative to the feed mass were obtained, until the imago developed.

As a control, leaves provided only with solvent and emulsifier of the stated concentration were used for feeding. The active compounds according to the invention, from the preparative examples, showed a good activity in this test.

EXAMPLE 2

Growth-Inhibiting/Contact Test

Test insects: *Dysdercus intermedius* (larvae in the 3rd stage of development) — 10 specimens
Feedstuff: cottonseeds (*Gossypium hirsutum*)
Solvent: 4 parts by weight of acetone
Emulsifier: 1 part by weight of alkylaryl polyglycol ether To produce a suitable preparation of active compound, 2 parts by weight of active compound were mixed with the stated amount of solvent and emulsifier and with sufficient water to give a 1% strength mixture, which was diluted with water to the desired concentration.

The test insects were dipped for 3 seconds into active compound mixture of the chosen concentration and were then kept in cages and fed with untreated cottonseeds and water.

As a control, insects which had only been dipped in solvent and emusifier were kept and fed in the same manner. The active compounds according to the invention, from the preparative examples, showed a good action in this test.

EXAMPLE 3

Growth-Inhibiting/Mosquito Test

Test insects: *Aedes aegypti* (larvae in the 3rd stage of development) — 20 specimens
Solvent: 10 parts by weight of acetone
Emulsifier: 1 part by weight of polyoxyethylene-(20)-sorbitan monolaurate To produce a suitable preparation of active compound, 2 parts by weight of active compound were mixed with the stated amount of solvent and emulsifier and with sufficient water to give a mixture containing 100 ppm, which was diluted with water to the desired concentration.

The test insects were placed in 90 ml of these solutions of active compound and observed until the imago hatched. As a control, test insects were introduced into a mixture of solvent and emulsifier in water, of the stated concentration, and observed until the image hatched.

The active compounds according to the invention, from the preparative examples, showed a good activity in this test.

EXAMPLE 4

Pellicularia test

Solvent: 11.75 parts by weight of acetone
Dispersing agent: 0.75 parts by weight of alkylaryl polyglycol ether
Water 987.5 parts by weight of water The amount of active compound required for the desired concentration in the spray liquor was mixed with the stated amount of the solvent and of the dispersing agent and the concentrate was diluted with the stated amount of water.

2 × 30 rice plants about 2-4 weeks old were sprayed with the spray liquor until dripping wet. The plants remained in a greenhouse at temperatures of 22° to 24° C. and a relative atmospheric humidity of about 70% until they were dry. The plants were infected with a culture, grown on malt agar, of *Pellicularia sasakii*, and were set up at 28° to 30° and 100% relative atmospheric humidity.

The infection was determined after 5 to 8 days on the leaf sheaths in comparison to the untreated but infected control.

The active compounds according to the invention, from the preparative examples, showed a good activity in this test.

EXAMPLE 5

Mycelium growth test

Nutrient medium used:
20 parts by weight of agar-agar
200 parts by weight of potato decoction
5 parts by weight of malt
15 parts by weight of dextrose
5 parts by weight of peptone
2 parts by weight of $Na_2HPO_4$
0.3 part by weight of $Ca(NO_3)_2$
Composition of the solvent mixture:
0.19 part by weight of DMF
0.01 part by weight of emulsifier (alkylaryl polyglycol ether)
1.80 parts by weight of water
Ratio of solvent mixture to nutrient medium:
2 parts by weight of solvent mixture
100 parts by weight of agar nutrient medium The amount of active compound required for the desired active compound concentration in the nutrient medium was mixed with the stated amount of solvent mixture. The concentrate was thoroughly mixed, in the stated proportion, with the liquid nutrient medium (which had been cooled to 42° C.) and was then poured into Petri dishes of 9 cm diameter. Control plates to which the preparation had not been added were also set up.

When the nutrient medium had cooled and solidified, the plates were inoculated with the species of fungi stated in the following table and incubated at about 21° C.

Evaluation was carried out after 4–10 days, dependent upon the speed of growth of the fungi. When evaluation was carried out the radial growth of the mycelium on the treated nutrient media was compared with the growth on the control nutrient medium. In the evaluation of the fungus growth, the following characteristic values were used:
1 no fungus growth
up to 3 very strong inhibition of growth
up to 5 medium inhibition of growth
up to 7 slight inhibition of growth
9 growth equal to that of untreated control.

The active compounds, the active compound concentrations and the results can be seen from the following table:

Table 1

| Active compounds | Active compound concentration ppm | Mycelium growth test — Fungi |||||||||||||
|---|---|---|---|---|---|---|---|---|---|---|---|---|---|---|
| | | Sclerotinia sclerotiorum | Fusarium nivale | Rhizoctonia solani | Pythium ultimum | Cochliobolus miyabeanus | Botrytis cinerea | Verticillium alboatrum | Pyricularia oryzae | Phialophora cinerescens | Helminthosporium gramineum | Mycosphaerella musicola | Phytophthora cactorum | Pellicularia sasakii |
| $\begin{array}{c}CH_2-NH-CS-S\\ \phantom{CH_2-NH-CS-S}\diagdown Zn\ (known)\\ CH_2-NH-CS-S\diagup\end{array}$ | 10 | 9 | 9 | 9 | 9 | 9 | 9 | 9 | 9 | 9 | 5 | 5 | 9 | 9 |
| $\text{CH}_2\text{O}\!-\!\!\text{C}_6\text{H}_4\!-\!CH=N-C_{12}H_{25}$ (phenyl-CH₂O-C₆H₄-CH=N-C₁₂H₂₅) | | 1 | | 3 | 1 | 5 | | | 1 | | | | 1 | 1 |
| $\text{CH}_2\text{O}\!-\!\!\text{C}_6\text{H}_4\!-\!CH_2-NH-C_{12}H_{25}$ (20) | | 5 | | | | | 5 | | | 5 | | | 3 | 5 |
| $\text{CH}_2\text{O}\!-\!\!\text{C}_6\text{H}_4\!-\!CH=N-C_{16}H_{33}\text{-}n$ | | 1 | | 1 | 5 | 5 | 5 | 5 | 1 | | 1 | 1 | 1 | 3 |
| $\text{CH}_2\text{O}\!-\!\!\text{C}_6\text{H}_4\!-\!CH=N-C_{14}H_{29}\text{-}n$ | | 1 | 5 | 1 | 1 | 5 | 5 | 5 | 1 | | 1 | 1 | 1 | 1 |
| $CH_3\text{-}C_6H_3(CH_2O\text{-}C_6H_4\text{-}CH=N-C_{12}H_{25}\text{-}n)$ | | 5 | | 3 | 2 | 5 | 5 | 5 | 5 | | 3 | 3 | 3 | 3 |
| $Cl_2C_6H_3\text{-}CH_2O\text{-}C_6H_4\text{-}CH=N-C_{12}H_{25}\text{-}n$ (4-Cl 70% / 2-Cl 30%) | | 1 | | | 2 | | 3 | 5 | 1 | 1 | 3 | 1 | 3 | 3 |
| $Cl_2C_6H_3\text{-}CH_2O\text{-}C_6H_4\text{-}CH_2-NH-CH_2-CH(C_2H_5)-C_4H_9\text{-}n$ (70% 4-Cl / 30% 2-Cl) | | 1 | 5 | 3 | 2 | 5 | 3 | 5 | 5 | 1 | 3 | 5 | 1 | 3 |
| $\text{Ph-CH}_2\text{O-C}_6\text{H}_4\text{-}CH_2-NH-C_8H_{17}\text{-}n$ (16) | | 1 | 5 | 2 | 1 | 5 | 3 | 5 | 5 | 1 | 1 | | 2 | 3 |
| $\text{Ph-CH}_2\text{O-C}_6\text{H}_4\text{-}CH_2-NH-C_9H_{19}\text{-}n$ (18) | | | | | 2 | 5 | 3 | 5 | 3 | | | 2 | 2 | 3 |
| $\text{Cl-C}_6\text{H}_4\text{-CH}_2\text{O-C}_6\text{H}_4\text{-}CH=N-C_{12}H_{25}\text{-}n$ | | | | | | | | | | 5 | 5 | 2 | 1 | 1 |
| $\text{Cl-C}_6\text{H}_4\text{-CH}_2\text{O-C}_6\text{H}_4\text{-}CH_2-NH-C_{12}H_{25}\text{-}n$ (111) | | | | 3 | 1 | | | | 3 | | | 2 | 1 | 1 |

Table 1-continued

| Active compounds | Active compound concentration ppm | Mycelium growth test | | | | | | | Fungi | | | | |
|---|---|---|---|---|---|---|---|---|---|---|---|---|---|
| | | Sclerotinia sclerotiorum | Fusarium nivale | Rhizoctonia solani | Pythium ultimum | Cochliobolus miyabeanus | Botrytis cinerea | Verticillium albo-atrum | Pyricularia oryzae | Phialophora cinerescens | Helminthosporium gramineum | Mycosphaerella musicola | Phytophthora cactorum | Pellicularia sasakii |
|  | | 3 | | 3 | 3 | | 3 | 5 | 1 | 1 | | | 5 | 3 |

The preparation of the active compounds to be used according to this invention is illustrated by the following preparative examples.

EXAMPLE 6

(a) 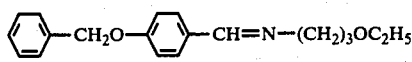

848 g (4 mol) of 4-benzyloxy-benzaldehyde, 480 g (4.66 mol) of 3-ethoxypropylamine and 1 g of p-toluenesulphonic acid in 2.5 l of toluene were heated for about 5 hours under reflux, using a water separator, until the elimination of water had ceased. After cooling the mixture, the p-toluenesulphonic acid was filtered off, the solvent was distilled off on a rotary evaporator and the crude product was fractionally distilled in vacuo.

996 g (84%) of [4-benzyloxy-benzylidene]-3-ethoxy-propylamine were obtained (boiling point = 197° C./0.4 mm Hg, $n_D^{20}$ = 1.5700).

(b) 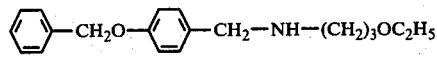 (1)

891 g (3 mol) of the compound from Example 6(a) in 1.0 l of ethanol were added dropwise to 64.3 g (1.7 mol) of NaBH$_4$ in 1.6 l of ethanol, while cooling with ice, at a rate of addition such that the reaction temperature was between 15° and 20° C. The mixture was then stirred for 2 hours at room temperature and 2 hours at 70° C., 300 ml of acetone were added dropwise to destroy the excess NaBH$_4$ and the solvent was distilled off as far as possible. The residue was mixed with 2 l of water and extracted three times with 1.2 l of toluene, the solvent was distilled off on a rotary evaporator and the crude product was fractionally distilled in vacuo. 825 g (92%) of [4-benzyloxy-benzyl]-3-ethoxy-propylamine were obtained; (boiling point = 181°–184° C./0.2 mm Hg, $n_D^{20}$ = 1.5468).

EXAMPLE 7

(a) 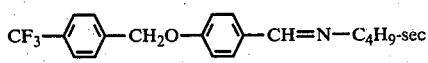

28.5 g of 4-(4-trifluoromethyl-benzyloxy)-benzaldehyde (0.1 mol), 0.1 g of p-toluenesulphonic acid and 7.5 g (0.1 mol) of sec.-butylamine in 120 ml of toluene were heated for 5 hours under reflux, the mixture was filtered and the solvent was distilled off in vacuo.

34 g of crude [4-(4-trifluoromethyl-benzyloxy)-benzylidene]-1-methyl-propylamine were isolated. The crude product was immediately reacted to give the corresponding amine.

(b) 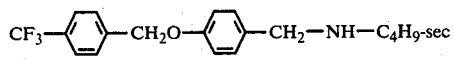 (2)

34 g of the compound from Example 7(a), dissolved in 100 ml of ethanol, were added dropwise to 3 g (0.08 mol) of NaBH$_4$ in 100 ml of ethanol at 15°–20° C. The mixture was then stirred for 2 hours at 25° C. and 2 hours at 70° C., 30 ml of acetone were added dropwise, the solvent was distilled off, 100 ml of water were added to the residue and the mixture was extracted by shaking three times with 150 ml of toluene each time.

The toluene phase was dried with Na$_2$SO$_4$ and filtered, the toluene was distilled off in vacuo and the crude product was fractionally distilled in vacuo.

27 g (79%, relative to 4-(4-trifluoromethyl-benzyloxy)-benzaldehyde) of the compound [4-(4-trifluoromethyl-benzyloxy)-benzyl]-1-methyl-propylamine were obtained (boiling point = 174° C./0.2 mm Hg; $n_D^{20}$ = 1.5113).

EXAMPLE 8

(a) 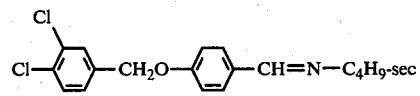

984 g (3.5 mol) of 4-(3,4-dichlorobenzyloxy)-benzaldehyde and 300 g (4.1 mol) of sec.-butylamine were heated for 1.5 hours under reflux. The water formed was then distilled off until the temperature in the reaction vessel had risen to 140° C. The crude product was fractionally distilled in vacuo.

955 g (81%) of [4-(3,4-dichlorobenzyloxy)-benzylidene]-1-methyl-propylamine were obtained (boiling point = 195° C./0.7 mm Hg, $n_D^{20}$ = 1.5870).

(b) 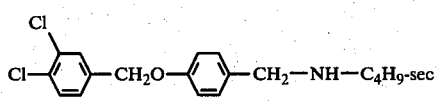 (3)

940 g (2.8 mol) of the compound from Example 8(a) were added dropwise to 56.6 g (1.5 mol) of NaBH$_4$ in 1.4 l of ethanol at 15° to 20° C., while cooling with ice. The mixture was then stirred for 2 hours at 25° C. and 2 hours at 60° C., 300 ml of acetone were added dropwise and the solvent was distilled off as far as possible. 2 l of H$_2$O were added to the residue and the mixture was extracted three times with 1.5 l of toluene at a time. The toluene phase was dried with Na$_2$SO$_4$, the solvent was distilled off in vacuo and the crude product was fractionally distilled in vacuo.

750 g (79%) of [4-(3,4-dichloro-benzyloxy)-benzyl]-1-methyl-propylamine were obtained (boiling point = 197° C./0.15 mm Hg, $n_D^{20}$ = 1.5660).

EXAMPLE 9

(a) 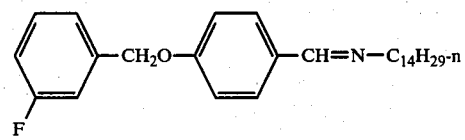

23 g (0.1 mol) of 4-(3-fluoro-benzyloxy)-benzaldehyde, 21.3 g (0.1 mol) of tetradecylamine and 0.1 g of p-toluenesulphonic acid in 180 ml of toluene were heated for 5 hours under a water separator, the catalyst was filtered off, the solvent was distilled off in vacuo and the crude product was recrystallized from ethanol.

37 g (87%) of [4-(3-fluoro-benzyloxy)-benzylidene)]-tetradecylamine were obtained (melting point = 58° C.).

(b) 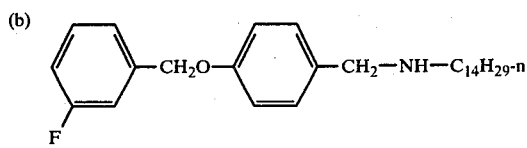 (4)

24 g (0.056 mol) of the compound from 9(a), in 100 ml of ethanol, were added dropwise to 1.2 g of NaBH$_4$ (0.03 mol) in 100 ml of ethanol at 15° to 20° C., the mixture was stirred for a further 2 hours at room temperature and 2 hours at 70° C., the solvent was distilled off, 100 ml of H$_2$O were added, the mixture was extracted by shaking three times with 150 ml of toluene at a time, the toluene was distilled off and the crude product was recrystallized from ethanol.

20 g (83%) of [4-(3-fluoro-benzyloxy)-benzyl]-tetradecylamine were obtained (melting point = 58° C.).

EXAMPLE 10

(a) 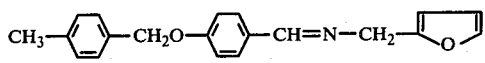

80 g (0.35 mol) of [4-(4-methyl-benzyloxy)]-benzaldehyde and 34.4 g (0.35 mol) of furfurylamine in 250 ml of toluene were heated for 5 hours under reflux, using a water separator, the solvent was distilled off in vacuo and the crude product was recrystallized from isopropanol.

100 g (93%) of [4-(4-methyl-benzyloxy)-benzylidene]-furfurylamine were obtained (melting point = 71° C.).

(b) 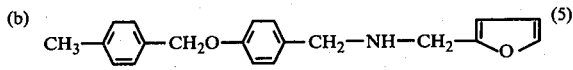 (5)

50 g (0.164 mol) of the compound from Example 10(a), in 100 ml of ethanol, were added dropwise to 4 g of NaBH$_4$ in 100 ml of ethanol. The mixture was then further stirred for 2 hours at room temperature and 2 hours at 70° C., the solvent was distilled off, 250 ml of water were added to the residue, the mixture was extracted by shaking three times with 250 ml of toluene at a time, the toluene was distilled off and the crude product was recrystallized from petroleum ether.

41 g (81%) of [4-(4-methyl-benzyloxy-benzyl]-furfurylamine were obtained; (melting point = 57° C.).

EXAMPLE 11

(a) 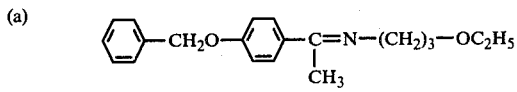

0.3 mol (67.8 g) of 4-benzyloxy-acetophenone and 30.9 g of 3-ethoxypropylamine were heated with 0.1 g of p-toluene-sulphonic acid in 500 ml of xylene for 5 hours under reflux, using a water separator, the catalyst was filtered off and the solution was concentrated to 300 ml by evaporation.

(b) 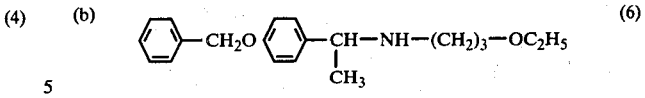 (6)

20 g of Raney nickel were added to the xylene solution of the Schiff's base, obtained according to Example 11(a), and the base was reduced for 5 hours at 90° C. under a H$_2$ pressure of 100 bars. After releasing the pressure, the catalyst was filtered off, the solvent was distilled off in vacuo and the crude product was fractionally distilled in vacuo.

70 g (74%, based on the acetophenone) of [(4-benzyloxy)-benzyl-α-methyl)]-3-ethoxy-propylamine were obtained (boiling point = 196° C./0.7 mm Hg; n$_D^{20}$ = 1.5445).

EXAMPLE 12

(a) 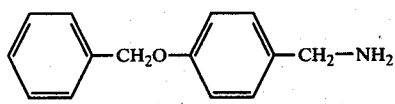

212 g (1 mol) of 4-benzyloxy-benzaldehyde, 500 ml of methanol, 200 ml of liquid ammonia, 2 ml of glacial acetic acid and 40 g of Raney nickel were heated in an autoclave to 100° C. for 1 hour. The product was then reduced for 2 hours at 90°–100° C. under a hydrogen pressure of 100 bars. After releasing the pressure, the catalyst was filtered off and the crude product was distilled in vacuo.

150 g (70%) of 4-benzyloxy-benzylamine were obtained (boiling point = 173° C./0.2 mm Hg; melting point = 111°–114° C.).

(b) 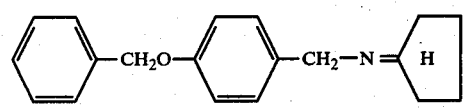

60 g (0.28 mol) of the compound from Example 12(a) in 150 ml of toluene and 25 g of cyclopentanone were heated for 4 hours under reflux, using a water separator, the solvent was distilled off and the crude product was recrystallized from cyclohexane.

66 g (84% of [4-benzyloxy-benzyl]-cyclopentylideneamine were obtained.

(c) 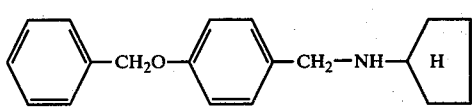 (7)

53 g (0.19 mol) of the compound from 7(b) in 150 ml of ethanol were added dropwise to 5 g (0.13 mol) of NaBH$_4$ in 150 ml of ethanol at 15° to 20° C. The mixture was then stirred for 2 hours at room temperature and 2 hours at 60° C., 50 ml of acetone were added dropwise and the solvent was distilled off. 200 ml of water were added to the crude product, the mixture was extracted by shaking three times with 200 ml of toluene at a time, the solvent was distilled off in vacuo and the crude product was fractionally distilled in vacuo.

Yield 40 g = 75% of (4-benzyloxy-benzyl)-cyclopentylamine (boiling point = 175°–177° C./0.3 mm Hg; $n_D^{20}$ = 1.5702).

The following compounds could be prepared analogously, the boiling points being given in ° C./mm Hg and solidification points (solid pt.).

Table 2

| Compound No. | Structure | Properties |
|---|---|---|
| 8. | Ph—CH$_2$O—C$_6$H$_4$—CH$_2$—NH—CH$_2$—CH=CH$_2$ | b.pt.161–162/0.15<br>$n_D^{20}$ 1.5723 |
| 9. | Ph—CH$_2$O—C$_6$H$_4$—CH$_2$—NH—C$_4$H$_9$-n | b.pt.170–172/0.6<br>solid.pt.31–33 |
| 10. | Ph—CH$_2$O—C$_6$H$_4$—CH$_2$—NH—C$_4$H$_9$-i | b.pt.162/0.1<br>$n_D^{20}$ 1.5505 |
| 11. | Ph—CH$_2$O—C$_6$H$_4$—CH$_2$—NH—C$_4$H$_9$-sec | b.pt.162–164/0.2<br>$n_D^{20}$ 1.5528 |
| 12. | Ph—CH$_2$O—C$_6$H$_4$—CH$_2$—NH—C$_4$H$_9$-t | b.pt.154–158/0.35<br>solid.pt.40–43 |
| 13. | Ph—CH$_2$O—C$_6$H$_4$—CH$_2$—NH—C(CH$_3$)$_2$—C$_2$H$_5$ | b.pt.168–170/0.1<br>$n_D^{20}$ 1.5475 |
| 14. | Ph—CH$_2$O—C$_6$H$_4$—CH$_2$—NH—C$_6$H$_{13}$-n | b.pt.170/0.2<br>solid.pt.35–37 |
| 15. | Ph—CH$_2$O—C$_6$H$_4$—CH$_2$—NH—C$_7$H$_{15}$-n | b.pt.184/0.15<br>$n_D^{20}$ 1.5373 |
| 16. | Ph—CH$_2$O—C$_6$H$_4$—CH$_2$—NH—C$_8$H$_{17}$-n | b.pt.242/4.2<br>solid.pt.43–45 |
| 17. | Ph—CH$_2$O—C$_6$H$_4$—CH$_2$—NH—CH$_2$—CH(C$_2$H$_5$)—C$_4$H$_9$-n | b.pt.188–192/0.5<br>$n_D^{20}$ 1.5370 |
| 18. | Ph—CH$_2$O—C$_6$H$_4$—CH$_2$—NH—C$_9$H$_{19}$-n | b.pt.216–218/0.4<br>solid.pt.40–42 |
| 19. | Ph—CH$_2$O—C$_6$H$_4$—CH$_2$—NH—CH$_2$CH$_2$—CH(CH$_3$)—CH(CH$_3$)—CH(CH$_3$)—CH$_3$ | b.pt.171/0.1<br>$n_D^{20}$ 1.5305 |
| 20. | Ph—CH$_2$O—C$_6$H$_4$—CH$_2$—NH—C$_{12}$H$_{25}$-n | b.pt.237–239/0.45<br>solid.pt.55–57 |
| 21. | Ph—CH$_2$O—C$_6$H$_4$—CH$_2$—NH—C$_{14}$H$_{29}$-n | solid.pt.59–61 |
| 22. | Ph—CH$_2$O—C$_6$H$_4$—CH$_2$—NH—C$_{16}$H$_{33}$-n | solid.pt.58–61 |

Table 2-continued

| Compound No. | Structure | Properties |
|---|---|---|
| 23. | C6H5—CH2O—C6H4—CH2—NH—C18H37-n | solid.pt.63–65 |
| 24. | C6H5—CH2O—C6H4—CH2—NH—CH2CH2—OH | solid.pt.44–46 |
| 25. | C6H5—CH2O—C6H4—CH2—NH—CH2CH2—OCH3 | b.pt.155/0.05<br>$n_D^{20}$ 1.5573 |
| 26. | C6H5—CH2O—C6H4—CH2—NH—(CH2)3—OCH3 | b.pt.169–170/0.15<br>$n_D^{20}$ 1.5545 |
| 27. | C6H5—CH2O—C6H4—CH2—NH—(CH2)3—OC2H5 | b.pt.181–184/0.2 (cf Ex 1)<br>$n_D^{20}$ 1.5468 |
| 28. | C6H5—CH2O—C6H4—CH2—NH—(CH2)3—O—C4H9-n | b.pt.186/0.1<br>$n_D^{20}$ 1.5361 |
| 29. | C6H5—CH2O—C6H4—CH2—NH—(CH2)3—N(C2H5)2 | b.pt.188/0.2<br>$n_D^{20}$ 1.5430 |
| 30. | C6H5—CH2O—C6H4—CH2—NH—(CH2)3—N(CH3)2 | |
| 31. | C6H5—CH2O—C6H4—CH2—NH—C5H9 (cyclopentyl) | b.pt.175–177/0.3 (cf Ex 7)<br>$n_D^{20}$ 1.5702 |
| 32. | C6H5—CH2O—C6H4—CH2—NH—C6H11 (cyclohexyl) | b.pt.178/0.12<br>solid.pt.31–33 |
| 33. | C6H5—CH2O—C6H4—CH2—NH—CH2—(2-furyl) | b.pt.202/0.15<br>$n_D^{20}$ 1.5835 |
| 34. | CH3—C6H4—CH2O—C6H4—CH2—NH—CH3 | |
| 35. | CH3—C6H4—CH2O—C6H4—CH2—NH—C2H5 | |
| 36. | CH3—C6H4—CH2O—C6H4—CH2—NH—C3H7-n | |
| 37. | CH3—C6H4—CH2O—C6H4—CH2—NH—C3H7-i | |
| 38. | CH3—C6H4—CH2O—C6H4—CH2—NH—C4H9-i | b.pt.175–180/0.4<br>solid.pt.42 |

Table 2-continued

| Compound No. | Structure | Properties |
|---|---|---|
| 39. | $CH_3$—⟨phenyl⟩—$CH_2O$—⟨phenyl⟩—$CH_2$—NH—$C_4H_9$-sec | b.pt.172/0.7 solid.pt.38–40 |
| 40. | $CH_3$—⟨phenyl⟩—$CH_2O$—⟨phenyl⟩—$CH_2$—NH—$C(CH_3)_2C_2H_5$ | solid.pt.73 |
| 41. | $CH_3$—⟨phenyl⟩—$CH_2O$—⟨phenyl⟩—$CH_2$—NH—$C_6H_{13}$-n | solid.pt.41 |
| 42. | $CH_3$—⟨phenyl⟩—$CH_2O$—⟨phenyl⟩—$CH_2$—NH—$C_7H_{15}$-n | |
| 43. | $CH_3$—⟨phenyl⟩—$CH_2O$—⟨phenyl⟩—$CH_2$—NH—$CH_2$—CH($C_2H_5$)—$C_4H_9$-n | b.pt /0.85 $n_D^{20}$ 1.5322 |
| 44. | $CH_3$—⟨phenyl⟩—$CH_2O$—⟨phenyl⟩—$CH_2$—NH—$C_{12}H_{25}$-n | solid.pt.59–60 |
| 45. | $CH_3$—⟨phenyl⟩—$CH_2O$—⟨phenyl⟩—$CH_2$—NH—$C_{14}H_{29}$-n | solid.pt.59 |
| 46. | $CH_3$—⟨phenyl⟩—$CH_2O$—⟨phenyl⟩—$CH_2$—NH—$CH_2CH_2$—OH | solid.pt. 65° |
| 47. | $CH_3$—⟨phenyl⟩—$CH_2O$—⟨phenyl⟩—$CH_2$—NH—$(CH_2)_3$—$OC_2H_5$ | b.pt.198–202/0.3 $n_D^{20}$ 1.5451 |
| 48. | $CH_3$—⟨phenyl⟩—$CH_2O$—⟨phenyl⟩—$CH_2$—NH—$(CH_2)_3$—N($CH_3)_2$ | |
| 49. | $CH_3$—⟨phenyl⟩—$CH_2O$—⟨phenyl⟩—$CH_2$—NH—$C(C_2H_5)_2$—C≡CH | |
| 50. | $CH_3$—⟨phenyl⟩—$CH_2O$—⟨phenyl⟩—$CH_2$—NH—⟨cyclohexyl-H⟩ | b.pt.230–234/2.2 solid.pt.45–46 |
| 51. | $CH_3$—⟨phenyl⟩—$CH_2O$—⟨phenyl⟩—$CH_2$—NH—⟨cyclohexyl(H)(C≡CH)⟩ | |
| 52. | $CH_3$—⟨phenyl⟩—$CH_2O$—⟨phenyl⟩—$CH_2$—NHCH$_2$—⟨furyl⟩ | solid.pt.45 (cf Ex 5) |
| 53. | ⟨3-CH$_3$-phenyl⟩—$CH_2O$—⟨phenyl⟩—$CH_2$—NH—$C_4H_9$-sec | b.pt.183/0.3 $n_D^{20}$ 1.5510 |

Table 2-continued

| Compound No. | Structure | Properties |
|---|---|---|
| 54. | 3-CH₃-C₆H₄-CH₂O-C₆H₄-CH₂-NH-C₆H₁₃-n | b.pt.180/0.2  n$_D^{20}$ 1.5411 |
| 55. | 3-CH₃-C₆H₄-CH₂O-C₆H₄-CH₂-NH-CH₂CH(C₂H₅)-C₄H₉-n | |
| 56. | 3-CH₃-C₆H₄-CH₂O-C₆H₄-CH₂-NH-C₁₂H₂₅-n | solid pt.49 |
| 57. | 3-CH₃-C₆H₄-CH₂O-C₆H₄-CH₂-NH-C₁₄H₂₉-n | solid pt.52 |
| 58. | 3-CH₃-C₆H₄-CH₂O-C₆H₄-CH₂NH-(CH₂)₃-OC₂H₅ | b.pt.200/1.5  n$_D^{20}$ 1.5435 |
| 59. | 3-CH₃-C₆H₄-CH₂O-C₆H₄-CH₂NH-CH₂-(2-furyl) | b.pt.197/0.35  n$_D^{20}$ 1.5784 |
| 60. | (CH₃)₂-C₆H₃-CH₂O-C₆H₄-CH₂-NH-C₄H₉-sec | |
| 61. | (CH₃)₂-C₆H₃-CH₂O-C₆H₄-CH₂-NH-C₆H₁₃-n | |
| 62. | (CH₃)₂-C₆H₃-CH₂O-C₆H₄-CH₂-NH-CH₂-CH(C₂H₅)-C₄H₉-n | |
| 63. | (CH₃)₂-C₆H₃-CH₂O-C₆H₄-CH₂-NH-C₁₂H₂₅-n | |
| 64. | (CH₃)₂-C₆H₃-CH₂O-C₆H₄-CH₂-NH-C₁₄H₂₉-n | |
| 65. | (CH₃)₂-C₆H₃-CH₂O-C₆H₄-CH₂-NH-(CH₂)₃OC₂H₅ | |
| 66. | (CH₃)₂-C₆H₃-CH₂O-C₆H₄-CH₂-NH-CH₂-(2-furyl) | |

Table 2-continued

| Compound No. | Structure |
|---|---|
| 67. | (CH₃)₃-C₆H₂-CH₂O-C₆H₄-CH₂-NH-C₄H₉-sec |
| 68. | (CH₃)₃-C₆H₂-CH₂O-C₆H₄-CH₂-NH-C₆H₁₃-n |
| 69. | (CH₃)₃-C₆H₂-CH₂O-C₆H₄-CH₂-NH-CH₂-CH(C₂H₅)-C₄H₉-n |
| 70. | (CH₃)₃-C₆H₂-CH₂O-C₆H₄-CH₂-NH-C₁₂H₂₅-n |
| 71. | (CH₃)₃-C₆H₂-CH₂O-C₆H₄-CH₂-NH-C₁₄H₂₉-n |
| 72. | (CH₃)₃-C₆H₂-CH₂O-C₆H₄-CH₂-NH-(CH₂)₃-OC₂H₅ |
| 73. | (CH₃)₃-C₆H₂-CH₂O-C₆H₄-CH₂-NH-CH₂-(2-furyl) |
| 74. | (CH₃)₄-C₆H-CH₂O-C₆H₄-CH₂NH-C₄H₉-sec |
| 75. | (CH₃)₄-C₆H-CH₂O-C₆H₄-CH₂-NH-C₆H₁₂-n |
| 76. | (CH₃)₄-C₆H-CH₂O-C₆H₄-CH₂-NH-C₁₂H₂₅-n |
| 77. | (CH₃)₄-C₆H-CH₂O-C₆H₄-CH₂-NH-(CH₂)₃OC₂H₅ |
| 78. | (CH₃)₄-C₆H-CH₂O-C₆H₄-CH₂-NH-CH₂-(2-furyl) |
| 79. | C₂H₅-C₆H₄-CH₂O-C₆H₄-CH₂-NH-C₄H₉sec |
| 80. | C₂H₅-C₆H₄-CH₂O-C₆H₄-CH₂-NH-C₆H₁₃-n |
| 81. | C₂H₅-C₆H₄-CH₂O-C₆H₄-CH₂-NH-C₁₂H₂₅-n |

Table 2-continued

| Compound No. | Structure | Properties |
|---|---|---|
| 82. | $C_2H_5$—⟨phenyl⟩—$CH_2O$—⟨phenyl⟩—$CH_2$—NH—$C_{14}H_{29}$-n | |
| 83. | $C_2H_5$—⟨phenyl⟩—$CH_2O$—⟨phenyl⟩—$CH_2$—NH—$(CH_2)_3OC_2H_5$ | |
| 84. | $C_2H_5$—⟨phenyl⟩—$CH_2O$—⟨phenyl⟩—$CH_2$—NH—$CH_2$—⟨furan⟩ | |
| 85. | $CH_3O$—⟨phenyl⟩—$CH_2O$—⟨phenyl⟩—$CH_2$—NH—$C_4H_9$-sec | b.pt.185–190/ 0.39 solid.pt.50–52 |
| 86. | $CH_3O$—⟨phenyl⟩—$CH_2O$—⟨phenyl⟩—$CH_2$—NH—$C_6H_{13}$-n | |
| 87. | $CH_3O$—⟨phenyl⟩—$CH_2O$—⟨phenyl⟩—$CH_2$—NH—$CH_2$—CH($C_2H_5$)—$C_4H_9$-n | |
| 88. | $CH_3O$—⟨phenyl⟩—$CH_2O$—⟨phenyl⟩—$CH_2$—NH—$C_7H_{15}$-n | |
| 89. | $CH_3O$—⟨phenyl⟩—$CH_2O$—⟨phenyl⟩—$CH_2$—NH—$C_{12}H_{25}$-n | |
| 90. | $CH_3O$—⟨phenyl⟩—$CH_2O$—⟨phenyl⟩—$CH_2$—NH—$C_{14}H_{29}$-n | solid.pt.70 |
| 91. | $CH_3O$—⟨phenyl⟩—$CH_2O$—⟨phenyl⟩—$CH_2NH$—$CH_2CH_2OH$ | |
| 92. | $CH_3O$—⟨phenyl⟩—$CH_2O$—⟨phenyl⟩—$CH_2NH$—$(CH_2)_3OC_2H_5$ | b.pt.200/ 0.28 $n_D^{20}$ 1.5481 |
| 93. | $CH_3O$—⟨phenyl⟩—$CH_2O$—⟨phenyl⟩—$CH_2$—NH—⟨cyclohexyl-H⟩ | |
| 94. | $CH_3O$—⟨phenyl⟩—$CH_2O$—⟨phenyl⟩—$CH_2$—NH—$CH_2$—⟨furan⟩ | |
| 95. | $C_2H_5$—O—⟨phenyl⟩—$CH_2O$—⟨phenyl⟩—$CH_2$—NH—$C_4H_9$-sec | |
| 96. | $C_2H_5O$—⟨cyclohexyl⟩—$CH_2O$—⟨phenyl⟩—$CH_2NH$—$C_6H_{13}$-n | |
| 97. | $C_2H_5O$—⟨phenyl⟩—$CH_2O$—⟨phenyl⟩—$CH_2NH$—$CH_2$—CH($C_2H_5$)—$C_4H_9$-n | |

Table 2-continued

| Compound No. | Structure | Properties |
|---|---|---|
| 98. | $C_2H_5O$—⟨C$_6$H$_4$⟩—$CH_2O$—⟨C$_6$H$_4$⟩—$CH_2$—NH—$C_{12}H_{25}$-n | |
| 99. | $C_2H_5O$—⟨C$_6$H$_4$⟩—$CH_2O$—⟨C$_6$H$_4$⟩—$CH_2$—NH—$C_{14}H_{29}$-n | |
| 100. | $C_2H_5O$—⟨C$_6$H$_4$⟩—$CH_2O$—⟨C$_6$H$_4$⟩—$CH_2$—NH—$(CH_2)_3OC_2H_5$ | |
| 101. | $C_2H_5O$—⟨C$_6$H$_4$⟩—$CH_2O$—⟨C$_6$H$_4$⟩—$CH_2$—NHCH$_2$—(furyl) | |
| 102. | Cl—⟨C$_6$H$_4$⟩—$CH_2O$—⟨C$_6$H$_4$⟩—$CH_2$NH—$CH_3$ | |
| 103. | Cl—⟨C$_6$H$_4$⟩—$CH_2O$—⟨C$_6$H$_4$⟩—$CH_2$NH—$C_2H_5$ | |
| 104. | Cl—⟨C$_6$H$_4$⟩—$CH_2O$—⟨C$_6$H$_4$⟩—$CH_2$—NH—$C_3H_7$-n | |
| 105. | Cl—⟨C$_6$H$_4$⟩—$CH_2O$—⟨C$_6$H$_4$⟩—$CH_2$—NH—$C_3H_7$-i | |
| 106. | Cl—⟨C$_6$H$_4$⟩—$CH_2O$—⟨C$_6$H$_4$⟩—$CH_2$—NH—$C_4H_9$-i | |
| 107. | Cl—⟨C$_6$H$_4$⟩—$CH_2O$—⟨C$_6$H$_4$⟩—$CH_2$—NH—$C_4H_9$-sec | solid.pt.41–42 |
| 108. | Cl—⟨C$_6$H$_4$⟩—$CH_2O$—⟨C$_6$H$_4$⟩—$CH_2$—NH—C(CH$_3$)$_2$—$C_2H_5$ | solid pt.78–80 |
| 109. | Cl—⟨C$_6$H$_4$⟩—$CH_2O$—⟨C$_6$H$_4$⟩—$CH_2$—NH—$C_6H_{13}$-n | b.pt.205–207/0.7 solid.pt.39–41 |
| 110. | Cl—⟨C$_6$H$_4$⟩—$CH_2O$—⟨C$_6$H$_4$⟩—$CH_2$—NH—CH$_2$—CH($C_2H_5$)—$C_4H_9$-n | b.pt.220/0.5 $n_D^{20}$ 1.5422 |
| 111. | Cl—⟨C$_6$H$_4$⟩—$CH_2O$—⟨C$_6$H$_4$⟩—$CH_2$—NH—$C_{12}H_{25}$-n | solid.pt.65–66 |
| 112. | Cl—⟨C$_6$H$_4$⟩—$CH_2O$—⟨C$_6$H$_4$⟩—$CH_2$—NH—$C_{14}H_{29}$-n | solid.pt.63 |
| 113. | Cl—⟨C$_6$H$_4$⟩—$CH_2O$—⟨C$_6$H$_4$⟩—$CH_2$—NH—$C_2H_4$—OH | |

Table 2-continued

| Compound No. | Structure | Properties |
|---|---|---|
| 114. | 4-Cl-C6H4-CH2O-C6H4-CH2-NH-(CH2)3-OC2H5 | b.pt. 212–214/0.4<br>$n_D^{20}$ 1.5532 |
| 115. | 4-Cl-C6H4-CH2O-C6H4-CH2-NH-cyclohexyl | solid.pt. 59–61 |
| 116. | 4-Cl-C6H4-CH2O-C6H4-CH2-NH-CH2-(2-furyl) | b.pt. 222/0.2<br>solid.pt. 36 |
| 117. | 2,3-Cl2-C6H3-CH2O-C6H4-CH2-NH-C4H9-sec | b.pt. 191/0.7<br>$n_D^{20}$ 1.5710 |
| 118. | 2,3-Cl2-C6H3-CH2O-C6H4-CH2-NH-CH2CH(C2H5)-C4H9-n | $n_D^{20}$ 1.5504 |
| 119. | 2,3-Cl2-C6H3-CH2O-C6H4-CH2-NH-CH2-CH(C2H5)-C4H9-n · HCl | solid.pt. 149 |
| 120. | 2,3-Cl2-C6H3-CH2O-C6H4-CH2-NH(CH2)3-OC2H5 | $n_D^{20}$ 1.5641 |
| 121. | 2,3-Cl2-C6H3-CH2O-C6H4-CH2-NH-C12H25-n | solid.pt. 34–36 |
| 122. | 2,3-Cl2-C6H3-CH2O-C6H4-CH2-NH-cyclohexyl | |
| 123. | 3,4-Cl2-C6H3-CH2O-C6H4-CH2-NH-C4H9-sec | b.pt. 176/0.15 (cf Ex 3)<br>$n_D^{20}$ 1.5660 |
| 124. | 3,4-Cl2-C6H3-CH2O-C6H4-CH2-NH-C6H13-n | |
| 125. | 3,4-Cl2-C6H3-CH2O-C6H4-CH2-NH-C7H15-n | |
| 126. | 3,4-Cl2-C6H3-CH2O-C6H4-CH2-NH-CH2-CH(C2H5)-C4H9-n | |

Table 2-continued

| Compound No. | Structure | |
|---|---|---|
| 127. | 3,4-Cl₂-C₆H₃-CH₂O-C₆H₄-CH₂-NH-C₁₂H₂₅-n | |
| 128. | 3,4-Cl₂-C₆H₃-CH₂O-C₆H₄-CH₂-NH-C₁₄H₂₉-n | |
| 129. | 3,4-Cl₂-C₆H₃-CH₂O-C₆H₄-CH₂-NH-CH₂CH₂-OH | |
| 130. | 3,4-Cl₂-C₆H₃-CH₂O-C₆H₄-CH₂-NH-(CH₂)₃-OC₂H₅ | |
| 131. | 3,4-Cl₂-C₆H₃-CH₂O-C₆H₄-CH₂-NH-C₆H₁₁ (cyclohexyl) | |
| 132. | 3,4-Cl₂-C₆H₃-CH₂O-C₆H₄-CH₂-NH-CH₂-(2-furyl) | |
| 133. | 2,6-Cl₂-C₆H₃-CH₂O-C₆H₄-CH₂NH-C₄H₉-sec | b.pt.210/0.45  n$_D^{20}$ 1.5679 |
| 134. | 2,6-Cl₂-C₆H₃-CH₂O-C₆H₄-CH₂-NH-C₆H₁₃-n | |
| 135. | 2,6-Cl₂-C₆H₃-CH₂O-C₆H₄-CH₂-NHCH₂-CH(C₂H₅)-C₄H₉-n | |
| 136. | 2,6-Cl₂-C₆H₃-CH₂O-C₆H₄-CH₂-NHC₂₂H₂₅-n | |
| 137. | 2,6-Cl₂-C₆H₃-CH₂O-C₆H₄-CH₂-NHC₁₄H₂₉-n | |

Table 2-continued

| Compound No. | Structure | Properties |
|---|---|---|
| 138. | 2,6-Cl₂-C₆H₃-CH₂O-C₆H₄-CH₂-NH-(CH₂)₃-OC₂H₅ | b.pt. 223/0.2 $n_D^{20}$ 1.5621 |
| 139. | 2,6-Cl₂-C₆H₃-CH₂O-C₆H₄-CH₂-NH-CH₂-(2-furyl) | |
| 140. | 4-F-C₆H₄-CH₂O-C₆H₄-CH₂-NH-C₄H₉-sec | |
| 141. | 4-F-C₆H₄-CH₂O-C₆H₄-CH₂-NH-C₆H₁₃-n | |
| 142. | 4-F-C₆H₄-CH₂O-C₆H₄-CH₂-NH-CH₂-CH(C₂H₅)-C₄H₉-n | |
| 143. | 4-F-C₆H₄-CH₂O-C₆H₄-CH₂-NH-C₇H₉-n | |
| 144. | 4-F-C₆H₄-CH₂O-C₆H₄-CH₂-NH-C₁₂H₂₅-n | |
| 145. | 4-F-C₆H₄-CH₂O-C₆H₄-CH₂-NH-C₁₄H₂₉-n | |
| 146. | 4-F-C₆H₄-CH₂O-C₆H₄-CH₂-NH-CH₂CH₂-OH | |
| 147. | 4-F-C₆H₄-CH₂O-C₆H₄-CH₂-NH-(CH₂)₃-O-C₂H₅ | |
| 148. | 4-F-C₆H₄-CH₂O-C₆H₄-CH₂-NH-cyclohexyl | |
| 149. | 4-F-C₆H₄-CH₂O-C₆H₄-CH₂-NH-CH₂-(2-furyl) | |
| 150. | 3-F-C₆H₄-CH₂O-C₆H₄-CH₂NH-C₄H₉-sec | b.p. 171°/0.3 $n_D^{20}$ 1.5365 |
| 151. | 3-F-C₆H₄-CH₂O-C₆H₄-CH₂-NH-C₆H₁₃-n | $n_D^{20}$ 1.5272 |

Table 2-continued

| Compound No. | Structure | Notes |
|---|---|---|
| 152. | 3-F-C$_6$H$_4$-CH$_2$O-C$_6$H$_4$-CH$_2$NH-CH$_2$CH(C$_2$H$_5$)-C$_4$H$_9$-n | |
| 153. | 3-F-C$_6$H$_4$-CH$_2$O-C$_6$H$_4$-CH$_2$-NH-C$_{12}$H$_{25}$-n | |
| 154. | 3-F-C$_6$H$_4$-CH$_2$O-C$_6$H$_4$-CH$_2$-NH-C$_{14}$H$_{29}$-n | solid.pt.58 (cf Ex 4) |
| 155. | 3-F-C$_6$H$_4$-CH$_2$O-C$_6$H$_4$-CH$_2$-NH-(CH$_2$)$_3$OC$_2$H$_5$ | $n_D^{20}$ 1.5360 |
| 156. | 3-F-C$_6$H$_4$-CH$_2$O-C$_6$H$_4$-CH$_2$-NH-CH$_2$-(2-furyl) | $n_D^{20}$ 1.5680 |
| 157. | 4-CF$_3$-C$_6$H$_4$-CH$_2$O-C$_6$H$_4$-CH$_2$-NH-C$_4$H$_9$-sec | b.pt.174/(cf Ex 2) 0.2 $n_D^{20}$ 1.5113 |
| 158. | 4-CF$_3$-C$_6$H$_4$-CH$_2$O-C$_6$H$_4$-CH$_2$-NH-C$_6$H$_{13}$-n | mp 32° |
| 159. | 4-CF$_3$-C$_6$H$_4$-CH$_2$O-C$_6$H$_4$-CH$_2$-NH-C$_7$H$_{15}$-n | |
| 160. | 4-CF$_3$-C$_6$H$_4$-CH$_2$O-C$_6$H$_4$-CH$_2$-NH-CH$_2$-CH(C$_2$H$_5$)-C$_4$H$_9$-n | |
| 161. | 4-CF$_3$-C$_6$H$_4$-CH$_2$O-C$_6$H$_4$-CH$_2$NH-C$_{12}$H$_{25}$-n | mp 46° |
| 162. | 4-CF$_3$-C$_6$H$_4$-CH$_2$O-C$_6$H$_4$-CH$_2$NH-C$_{14}$H$_{29}$-n | |
| 163. | 4-CF$_3$-C$_6$H$_4$-CH$_2$O-C$_6$H$_4$-CH$_2$-NH-CH$_2$CH$_2$OH | |
| 164. | 4-CF$_3$-C$_6$H$_4$-CH$_2$O-C$_6$H$_4$-CH$_2$-NH-(CH$_2$)$_3$OC$_2$H$_5$ | $n_D^{20}$ 1.5100 |
| 165. | 4-CF$_3$-C$_6$H$_4$-CH$_2$O-C$_6$H$_4$-CH$_2$NH-cyclohexyl | |

Table 2-continued

| Compound No. | Structure | |
|---|---|---|
| 166. | CF₃–C₆H₄–CH₂O–C₆H₄–CH₂–NH–CH₂–(2-furyl) | $n_D^{20}$ 1.5400 |
| 167. | CF₃O–C₆H₄–CH₂O–C₆H₄–CH₂–NH–C₄H₉-sec | $n_D^{20}$ 1.5039 |
| 168. | CF₃O–C₆H₄–CH₂O–C₆H₄–CH₂–NH–C₆H₁₃-n | |
| 169. | CF₃O–C₆H₄–CH₂O–C₆H₄–CH₂–NH–CH₂–CH(C₂H₅)–C₄H₉-n | |
| 170. | CF₃O–C₆H₄–CH₂O–C₆H₄–CH₂–C₁₂H₂₅-n | |
| 171. | CF₃O–C₆H₄–CH₂O–C₆H₄–CH₂–NH–C₁₄H₂₉-n | |
| 172. | CF₃O–C₆H₄–CH₂O–C₆H₄–CH₂–NH–(CH₂)₃OC₂H₅ | $n_D^{20}$ 1.5039 |
| 173. | CF₃O–C₆H₄–CH₂O–C₆H₄–CH₂–NH–CH₂–(2-furyl) | |
| 174. | CF₃S–C₆H₄–CH₂O–C₆H₄–CH₂–NH–C₄H₉-sec | |
| 175. | CF₃S–C₆H₄–CH₂O–C₆H₄–CH₂NH–C₆H₁₃-n | mp 32° |
| 176. | CF₃S–C₆H₄–CH₂O–C₆H₄–CH₂–NH–C₁₂H₂₅-n | |
| 177. | CF₃S–C₆H₄–CH₂O–C₆H₄–CH₂–NH–C₁₄H₂₉-n | solid.pt.60 |
| 178. | CF₃S–C₆H₄–CH₂O–C₆H₄–CH₂–NH–CH₂–CH(C₂H₉)–C₄H₉-n | |
| 179. | CF₃S–C₆H₄–CH₂O–C₆H₄–CH₂–NH–(CH₂)₃OC₂H₅ | |
| 180. | CF₃S–C₆H₄–CH₂O–C₆H₄–CH₂–NH–CH₂–(2-furyl) | |
| 181. | CF₃O–(3-Cl-C₆H₃)–CH₂O–C₆H₄–CH₂NH–C₄H₉-sec | |

Table 2-continued

| Compound No. | Structure | |
|---|---|---|
| 182. | 3-Cl-4-CF₃O-C₆H₃-CH₂O-C₆H₄-CH₂NH-C₆H₁₃-n | $n_D^{20}$ 1.5126 |
| 183. | 3-Cl-4-CF₃O-C₆H₃-CH₂O-C₆H₄-CH₂NH-C₁₂H₂₅-n | |
| 184. | 3-Cl-4-CF₃O-C₆H₃-CH₂O-C₆H₄-CH₂NH-C₁₄H₂₉-n | |
| 185. | 3-Cl-4-CF₃O-C₆H₃-CH₂O-C₆H₄-CH₂NH-CH₂-(2-furyl) | |
| 186. | 3-Cl-4-CF₃O-C₆H₃-CH₂O-C₆H₄-CH₂NH-(CH₂)₃OC₂H₅ | |
| 187. | 3-Cl-4-CF₃O-C₆H₃-CH₂O-C₆H₄-CH₂-NH-CH₂-CH(C₂H₅)-C₄H₉-n | |
| 188. | 3-CF₃-4-Cl-C₆H₃-CH₂O-C₆H₄-CH₂-NH-C₄H₉-sec | $n_D^{20}$ 1.5270 |
| 189. | 3-CF₃-4-Cl-C₆H₃-CH₂O-C₆H₄-CH₂-NH-C(CH₃)₂-C₂H₅ | |
| 190. | 3-CF₃-4-Cl-C₆H₃-CH₂O-C₆H₄-CH₂-NH-C(C₂H₅)₂-C≡CH | |
| 191. | 3-CF₃-4-Cl-C₆H₃-CH₂O-C₆H₄-CH₂NH-C₆H₁₃-n | $n_D^{20}$ 1.5212 |
| 192. | 3-CF₃-4-Cl-C₆H₃-CH₂O-C₆H₄-CH₂NH-C₇H₁₅-n | |
| 193. | 3-CF₃-4-Cl-C₆H₃-CH₂O-C₆H₄-CH₂NH-CH₂-CH(C₂H₅)-C₄H₉-n | |
| 194. | 3-CF₃-4-Cl-C₆H₃-CH₂O-C₆H₄-CH₂-NH-C₁₂H₂₅-n | mp 32-36° |

Table 2-continued

| Compound No. | Structure | |
|---|---|---|
| 195. | 4-CF$_3$-3-Cl-C$_6$H$_3$-CH$_2$O-C$_6$H$_4$-CH$_2$NH-C$_{14}$H$_{29}$-n | |
| 196. | 4-CF$_3$-3-Cl-C$_6$H$_3$-CH$_2$O-C$_6$H$_4$-CH$_2$NH-CH$_2$CH$_2$OH | |
| 197. | 4-CF$_3$-3-Cl-C$_6$H$_3$-CH$_2$O-C$_6$H$_4$-CH$_2$-NH-(CH$_2$)$_3$OC$_2$H$_5$ | $n_D^{20}$ 1.5209 |
| 198. | 4-CF$_3$-3-Cl-C$_6$H$_3$-CH$_2$O-C$_6$H$_4$-CH$_2$NH-(CH$_2$)$_3$-N(CH$_3$)$_2$ | |
| 199. | 4-CF$_3$-3-Cl-C$_6$H$_3$-CH$_2$O-C$_6$H$_4$-CH$_2$NH-cyclohexyl | $n_D^{20}$ 1.5521 |
| 200. | 4-CF$_3$-3-Cl-C$_6$H$_3$-CH$_2$O-C$_6$H$_4$-CH$_2$-NH-CH$_2$-(2-furyl) | $n_D^{20}$ 1.5790 |
| 201. | 4-CH$_3$-C$_6$H$_4$-CH$_2$O-(3,5-Br$_2$-C$_6$H$_2$)-CH$_2$NH-C$_4$H$_9$-sec | |
| 202. | 4-CH$_3$-C$_6$H$_4$-CH$_2$O-(3,5-Br$_2$-C$_6$H$_2$)-CH$_2$NH-C$_6$H$_{13}$-n | mp 60° |
| 203. | 4-CH$_3$-C$_6$H$_4$-CH$_2$O-(3,5-Br$_2$-C$_6$H$_2$)-CH$_2$NH-CH$_2$CH(C$_2$H$_5$)-C$_4$H$_9$-n | |
| 204. | 4-CH$_3$-C$_6$H$_4$-CH$_2$O-(3,5-Br$_2$-C$_6$H$_2$)-CH$_2$NH-C$_{12}$H$_{25}$-n | |
| 205. | 4-CH$_3$-C$_6$H$_4$-CH$_2$O-(3,5-Br$_2$-C$_6$H$_2$)-CH$_2$NH-C$_{14}$H$_{29}$-n | solid.pt.71 |

Table 2-continued
| Compound No. | | |
|---|---|---|
| 206. | 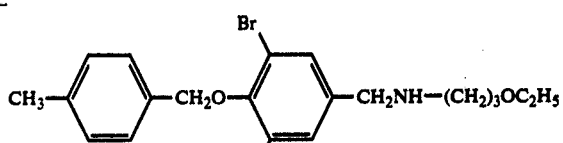 | |
| 207. | 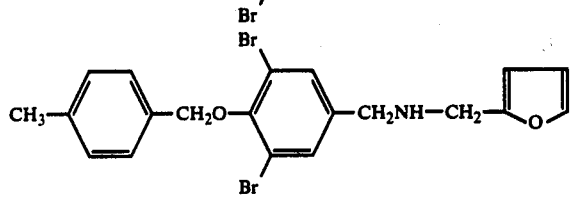 | |
| 208. | 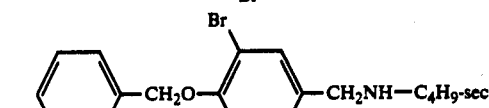 | |
| 209. | 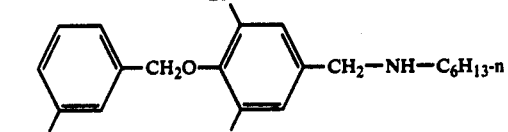 | $n_D^{20}$ 1.5520 |
| 210. | 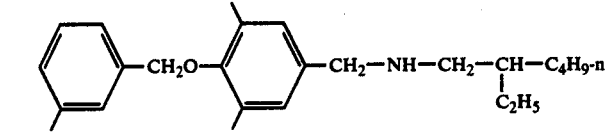 | |
| 211. | 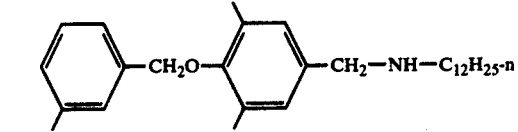 | |
| 212. | 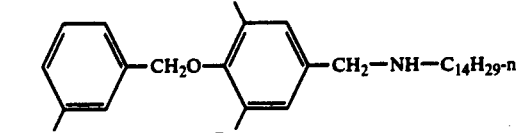 | |
| 213. | 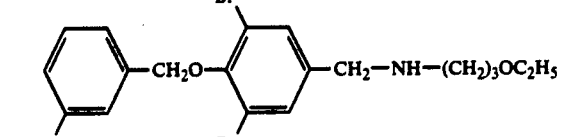 | |
| 214. | 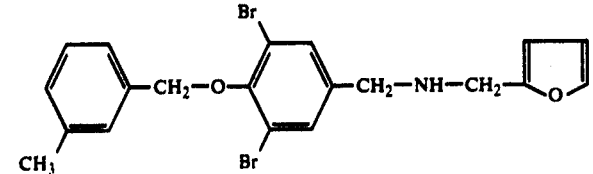 | |
| 215. | 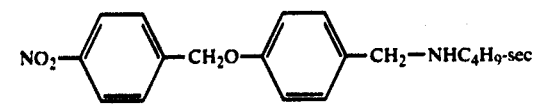 | |

Table 2-continued
| Compound No. | | |
|---|---|---|
| 216. | 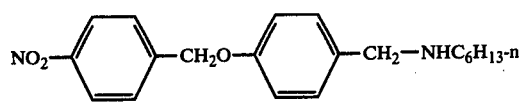 | |
| 217. | 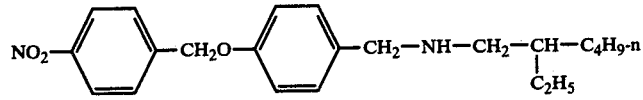 | |
| 218. | 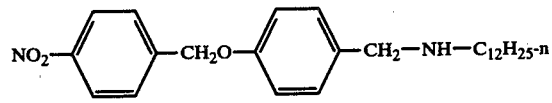 | |
| 219. | 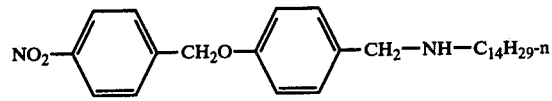 | |
| 220. |  | |
| 221. | 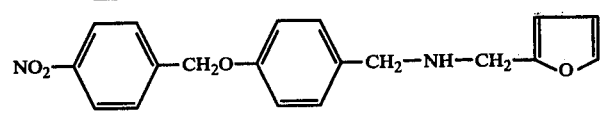 | |
| 222. | 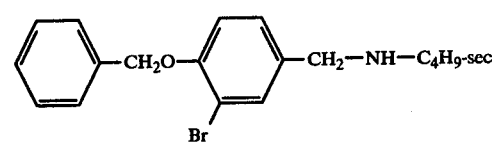 | |
| 223. | 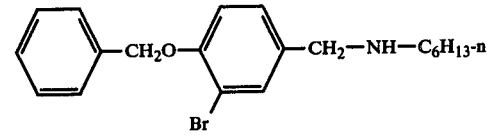 | $n_D^{20}$ 1.5604 |
| 224. | 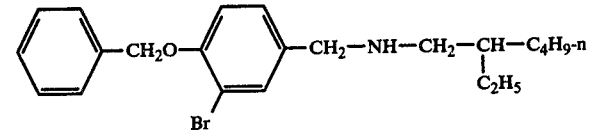 | |
| 225. | 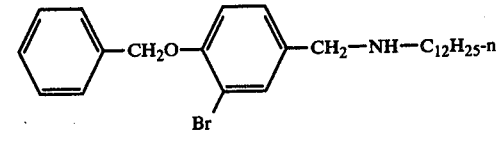 | |
| 226. | 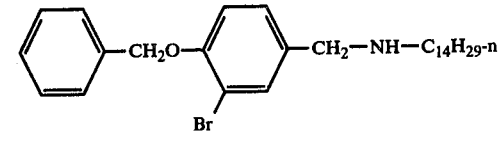 | |
| 227. | 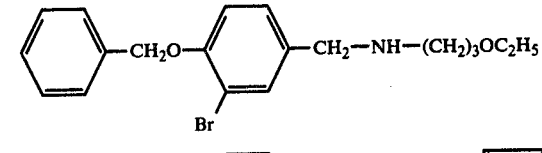 | |
| 228. | 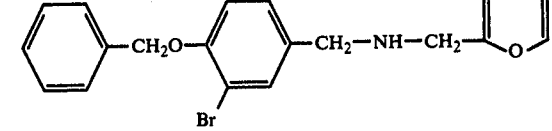 | |

Table 2-continued
| Compound No. | | |
|---|---|---|
| 229. | 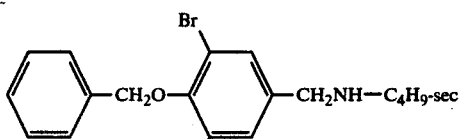 | $n_D^{20}$ 1.5846 |
| 230. | 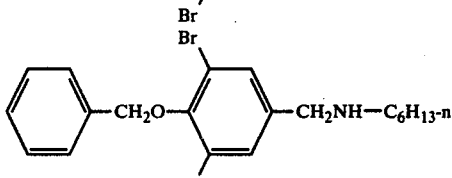 | |
| 231. | 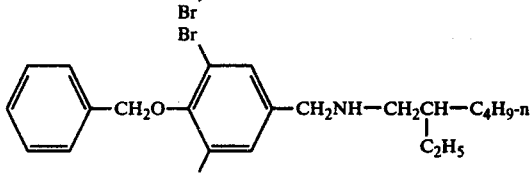 | |
| 232. | 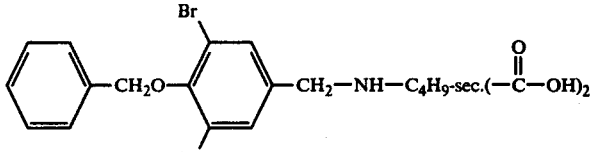 | |
| 233. | 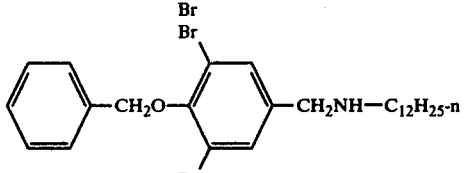 | |
| 234. | 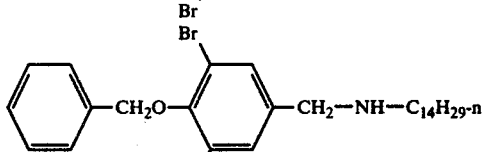 | |
| 235. | 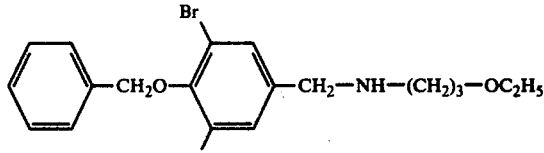 | $n_D^{20}$ 1.5757 |
| 236. | 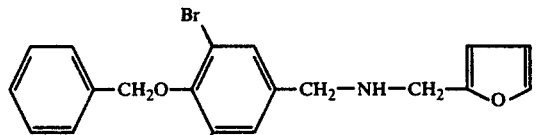 | |
| 237. | 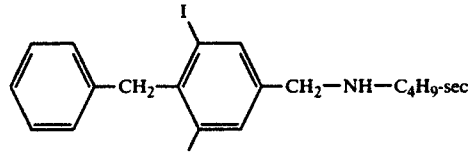 | |
| 238. | 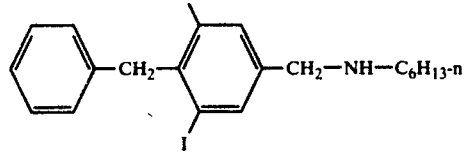 | |

Table 2-continued
| Compound No. | |
|---|---|
| 239. | 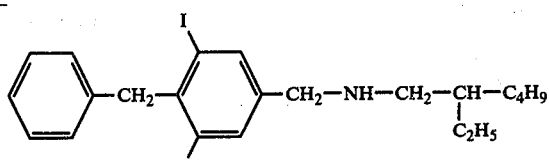 |
| 240. | 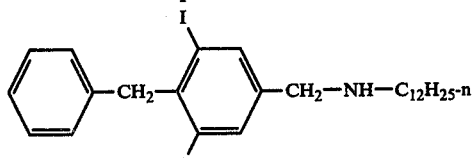 |
| 241. | 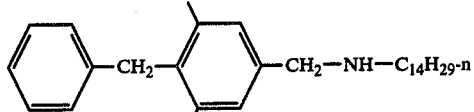 |
| 242. | 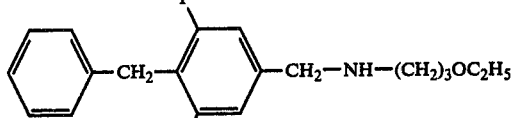 |
| 243. | 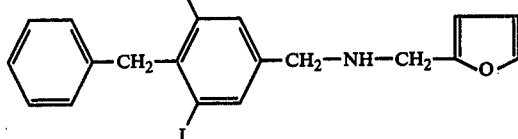 |
| 244. | 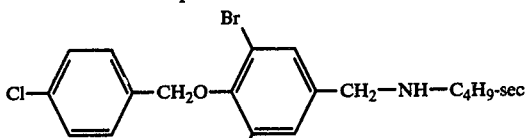 |
| 245. | 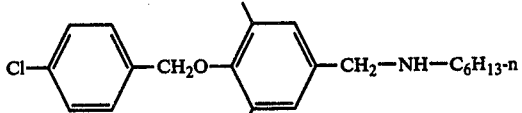 |
| 246. | 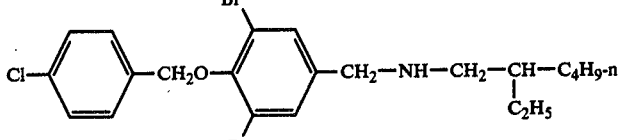 |
| 247. | 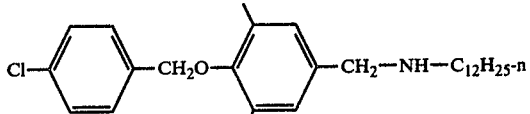 solid.pt.75 |
| 248. | 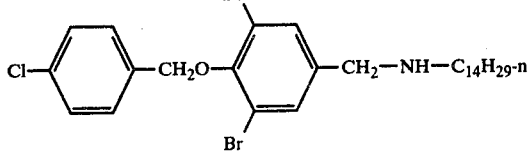 |

Table 2-continued
| Compound No. | Structure | |
|---|---|---|
| 249. | 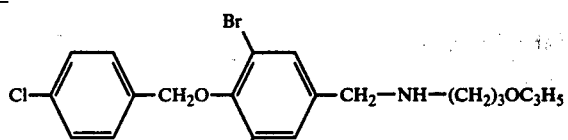 | |
| 250. | 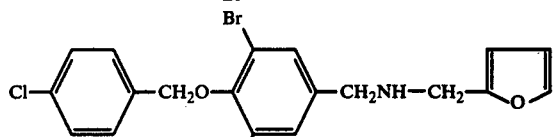 | |
| 251. | 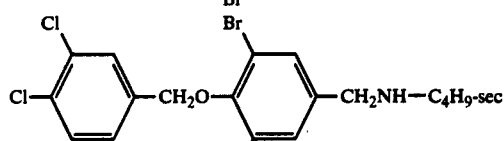 | |
| 252. | 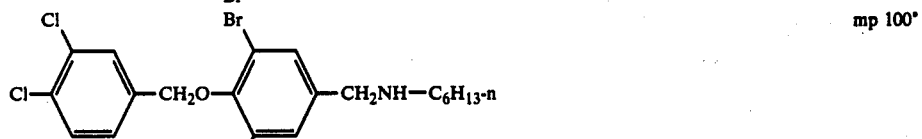 | mp 100° |
| 253. | 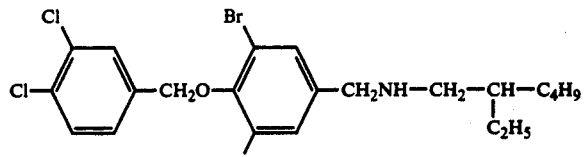 | |
| 254. | 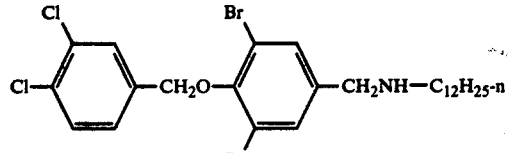 | |
| 255. | 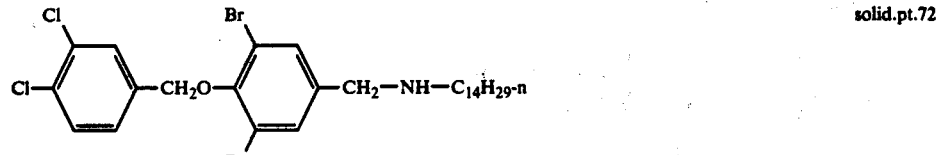 | solid.pt.72 |
| 256. | 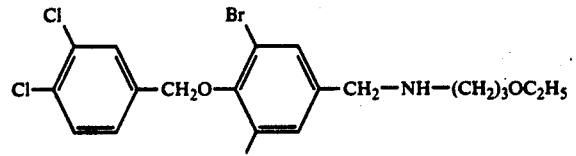 | |
| 257. | 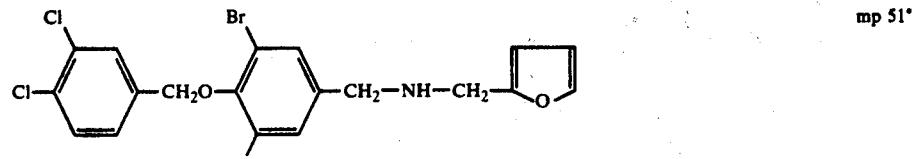 | mp 51° |
| 258. | 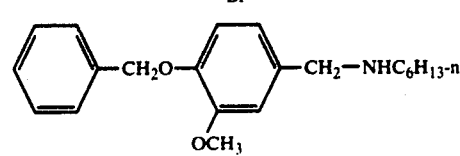 | |

Table 2-continued

| Compound No. | Structure | Properties |
|---|---|---|
| 259. | C₆H₅−CH₂O−(3-OCH₃-C₆H₃)−CH₂−NH−C₄H₉-sec | b.pt. 180–185/0.4; $n_D^{20}$ 1.5526 |
| 260. | C₆H₅−CH₂O−(3-OCH₃-C₆H₃)−CH₂−NH−CH₂CH(C₂H₅)−C₄H₉-n | |
| 261. | C₆H₅−CH₂O−(3-OCH₃-C₆H₃)−CH₂−NH−C₁₂H₂₅-n | |
| 262. | C₆H₅−CH₂O−(3-OCH₃-C₆H₃)−CH₂−NH−C₁₄H₂₉-n | |
| 263. | C₆H₅−CH₂O−(3-OCH₃-C₆H₃)−CH₂−NH−(CH₂)₃OC₂H₅ | $n_D^{20}$ 1.5484 |
| 264. | C₆H₅−CH₂O−(3-OCH₃-C₆H₃)−CH₂NH−CH₂−(2-furyl) | |
| 265. | 4-CH₃-C₆H₄−CH₂O−(3-OCH₃-C₆H₃)−CH₂NH−C₄H₉-sec | solid pt. 83–85 |
| 266. | 4-CH₃-C₆H₄−CH₂O−(3-OCH₃-C₆H₃)−CH₂−NH−C₆H₁₃-n | |
| 267. | 4-CH₃-C₆H₄−CH₂O−(3-OCH₃-C₆H₃)−CH₂−NH−CH₂−CH(C₂H₅)−C₄H₉-n | |
| 268. | 4-CH₃-C₆H₄−CH₂O−(3-OCH₃-C₆H₃)−CH₂−NH−C₁₂H₂₅-n | |
| 269. | 4-CH₃-C₆H₄−CH₂O−(3-OCH₃-C₆H₃)−CH₂−NH−C₁₄H₂₉-n | |

Table 2-continued

| Compound No. | Structure | |
|---|---|---|
| 270. | 4-CH₃-C₆H₄-CH₂O-(3-OCH₃-C₆H₃)-CH₂-NH-(CH₂)₃-OC₂H₅ | $n_D^{20}$ 1.5550 |
| 271. | 4-CH₃-C₆H₄-CH₂O-(3-OCH₃-C₆H₃)-CH₂-NH-CH₂-(2-furyl) | |
| 272. | 3,4-Cl₂-C₆H₃-CH₂O-(3-OCH₃-C₆H₃)-CH₂-NH-C₄H₉-sec | $n_D^{20}$ 1.5669 |
| 273. | 3,4-Cl₂-C₆H₃-CH₂O-(3-OCH₃-C₆H₃)-CH₂-NH-C₆H₁₃-n | |
| 274. | 3,4-Cl₂-C₆H₃-CH₂O-(3-OCH₃-C₆H₃)-CH₂-NH-CH₂-CH(C₂H₅)-C₄H₉-n | |
| 275. | 3,4-Cl₂-C₆H₃-CH₂O-(3-OCH₃-C₆H₃)-CH₂-NH-C₁₂H₂₅-n | |
| 276. | 3,4-Cl₂-C₆H₃-CH₂O-(3-OCH₃-C₆H₃)-CH₂-NH-C₁₄H₂₉-n | |
| 277. | 3,4-Cl₂-C₆H₃-CH₂O-(3-OCH₃-C₆H₃)-CH₂-NH-(CH₂)₃-OC₂H₅ | $n_D^{20}$ 1.5590 |
| 278. | 3,4-Cl₂-C₆H₃-CH₂O-(3-OCH₃-C₆H₃)-CH₂-NH-CH₂-(2-furyl) | |
| 279. | C₆H₅-CH₂O-C₆H₄-CH(CH₃)-NH-C₆H₁₃-n | |
| 280. | C₆H₅-CH₂O-C₆H₄-CH(CH₃)-NH-CH₂-CH(C₂H₅)-C₄H₉-n | |

Table 2-continued

| Compound No. | Structure | |
|---|---|---|
| 281. | C₆H₅—CH₂O—C₆H₄—CH(CH₃)—NH—C₁₂H₂₅-n | |
| 282. | C₆H₅—CH₂O—C₆H₄—CH(CH₃)—NH—C₁₄H₂₉-n | |
| 283. | C₆H₅—CH₂O—C₆H₄—CH(CH₃)—NH—(CH₂)₃—OC₂H₅ | b.pt.196/0.7 (cf Ex 6) n_D^20 1.5445 |
| 284. | C₆H₅—CH₂O—C₆H₄—CH(CH₃)—NH—CH₂-(2-furyl) | |
| 285. | C₆H₅—CH₂O—C₆H₄—CH(CH₃)—NH—C₆H₁₁ (cyclohexyl) | solid.pt. 79–81 |
| 286. | 4-CH₃-C₆H₄—CH₂O—C₆H₄—CH(CH₃)—NH—C₆H₁₃-n | b.pt.190/0.3 n_D^20 1.5344 |
| 287. | 4-CH₃-C₆H₄—CH₂O—C₆H₄—CH(CH₃)—NH—CH₂—CH(C₂H₅)—C₄H₉-n | |
| 288. | 4-CH₃-C₆H₄—CH₂O—C₆H₄—CH(CH₃)—NH—C₁₂H₂₅-n | |
| 289. | 4-CH₃-C₆H₄—CH₂O—C₆H₄—CH(CH₃)—NH—C₁₄H₂₉-n | |
| 290. | 4-CH₃-C₆H₄—CH₂O—C₆H₄—CH(CH₃)—NH—(CH₂)₃OC₂H₅ | b.pt.202–210/1 |
| 291. | 4-CH₃-C₆H₄—CH₂O—C₆H₄—CH(CH₃)—NH—CH₂-(2-furyl) | solid.pt.63 |
| 292. | 3-Cl-C₆H₄—CH₂O—C₆H₄—CH(CH₃)—NH—C₆H₁₃-n | |
| 293. | 3-Cl-C₆H₄—CH₂O—C₆H₄—CH(CH₃)—NH—CH₂—CH(C₂H₅)—C₄H₉-n | |
| 294. | 3-Cl-C₆H₄—CH₂O—C₆H₄—CH(CH₃)—NH—C₁₂H₂₅-n | |

Table 2-continued

| Compound No. | Structure |
|---|---|
| 295. | 3-Cl-C$_6$H$_4$-CH$_2$O-C$_6$H$_4$-CH(CH$_3$)-NH-C$_{14}$H$_{29}$-n |
| 296. | 3-Cl-C$_6$H$_4$-CH$_2$O-C$_6$H$_4$-CH(CH$_3$)-NH-(CH$_2$)$_3$-OC$_2$H$_5$ |
| 297. | 3-Cl-C$_6$H$_4$-CH$_2$O-C$_6$H$_4$-CH(CH$_3$)-NH-CH$_2$-(2-furyl) |
| 298. | 3,4-Cl$_2$-C$_6$H$_3$-CH$_2$O-C$_6$H$_4$-CH(CH$_3$)-NH-C$_6$H$_{13}$-n |
| 299. | 3,4-Cl$_2$-C$_6$H$_3$-CH$_2$O-C$_6$H$_4$-CH(CH$_3$)-NH-CH$_2$-CH(C$_2$H$_5$)-C$_4$H$_9$-n |
| 300. | 3,4-Cl$_2$-C$_6$H$_3$-CH$_2$O-C$_6$H$_4$-CH(CH$_3$)-NH-C$_{12}$H$_{25}$-n |
| 301. | 3,4-Cl$_2$-C$_6$H$_3$-CH$_2$O-C$_6$H$_4$-CH(CH$_3$)-NH-C$_{14}$H$_{29}$-n |
| 302. | 3,4-Cl$_2$-C$_6$H$_3$-CH$_2$O-C$_6$H$_4$-CH(CH$_3$)-NH-(CH$_2$)$_3$-OC$_2$H$_5$  $\quad n_D^{20}$ 1.5568 |
| 303. | 3,4-Cl$_2$-C$_6$H$_3$-CH$_2$O-C$_6$H$_4$-CH(CH$_3$)-NH-CH$_2$-(2-furyl) |
| 304. | 2,6-Cl$_2$-C$_6$H$_3$-CH$_2$O-C$_6$H$_4$-CH(CH$_3$)-NH-C$_6$H$_{13}$-n |
| 305. | 2,6-Cl$_2$-C$_6$H$_3$-CH$_2$O-C$_6$H$_4$-CH(CH$_3$)-NH-CH$_2$-CH(C$_2$H$_5$)-C$_4$H$_9$-n |

Table 2-continued

| Compound No. | Structure | Properties |
|---|---|---|
| 306. | 2,6-Cl$_2$-C$_6$H$_3$-CH$_2$O-C$_6$H$_4$-CH(CH$_3$)-NH-C$_{12}$H$_{25}$-n | |
| 307. | 2,6-Cl$_2$-C$_6$H$_3$-CH$_2$O-C$_6$H$_4$-CH(CH$_3$)-NH-C$_{14}$H$_{29}$-n | |
| 308. | 2,6-Cl$_2$-C$_6$H$_3$-CH$_2$O-C$_6$H$_4$-CH(CH$_3$)-NH-(CH$_2$)$_3$OC$_2$H$_5$ | |
| 309. | 2,6-Cl$_2$-C$_6$H$_3$-CH$_2$O-C$_6$H$_4$-CH(CH$_3$)-NH-CH$_2$-(2-furyl) | |
| 310. | 3-Cl-C$_6$H$_4$-CH$_2$O-C$_6$H$_4$-CH$_2$-NH-C$_4$H$_9$-i | |
| 311. | 3-Cl-C$_6$H$_4$-CH$_2$O-C$_6$H$_4$-CH$_2$-NH-C$_4$H$_9$-sec | |
| 312. | 3-Cl-C$_6$H$_4$-CH$_2$O-C$_6$H$_4$-CH$_2$-NH-C(CH$_3$)$_2$C$_2$H$_5$ | |
| 313. | 3-Cl-C$_6$H$_4$-CH$_2$O-C$_6$H$_4$-CH$_2$-NH-C$_6$H$_{13}$-n | bp 203° mp 35° 0.2 |
| 314. | 3-Cl-C$_6$H$_4$-CH$_2$O-C$_6$H$_4$-CH$_2$-NH-C$_7$H$_{15}$-n | |
| 315. | 3-Cl-C$_6$H$_4$-CH$_2$O-C$_6$H$_4$-CH$_2$-NH-C$_8$H$_{17}$-n | |
| 316. | 3-Cl-C$_6$H$_4$-CH$_2$O-C$_6$H$_4$-CH$_2$-NH-C$_9$H$_{19}$-n | |

Table 2-continued

| Compound No. | Structure | Properties |
|---|---|---|
| 317. | 3-Cl-C6H4-CH2O-C6H4-CH2-NH-CH2-CH(C2H5)-C4H9-n | bp 210° 0.2 |
| 318. | 3-Cl-C6H4-CH2O-C6H4-CH2-NH-C12H25-n | $n_D^{20}$ 1.5410 |
| 319. | 3-Cl-C6H4-CH2O-C6H4-CH2-NH-C14H29-n | |
| 320. | 3-Cl-C6H4-CH2O-C6H4-CH2NH-CH2CH2-OH | |
| 321. | 3-Cl-C6H4-CH2O-C6H4-CH2-NH-(CH2)3OC2H5 | |
| 322. | 3-Cl-C6H4-CH2O-C6H4-CH2-NH-cyclohexyl | KP$_{0.2}$ 205° |
| 323. | 3-Cl-C6H4-CH2O-C6H4-CH2-NH-(2-methylcyclohexyl) | |
| 324. | 3-Cl-C6H4-CH2O-C6H4-CH2-NH-(menthyl) | |
| 325. | 3-Cl-C6H4-CH2O-C6H4-CH2-NH-(pinanyl) | |
| 326. | 3-Cl-C6H4-CH2O-C6H4-CH2-NH-(3,3,5-trimethylcyclohexyl) | |
| 327. | 3-Cl-C6H4-CH2O-C6H4-CH2-NH-(1,5,5-trimethylcyclohex-1-enyl) | |

Table 2-continued
| Compound No. | |
|---|---|
| 328. | 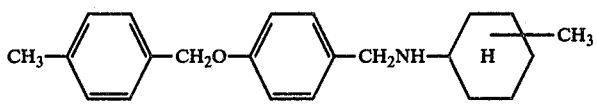 |
| 329. | 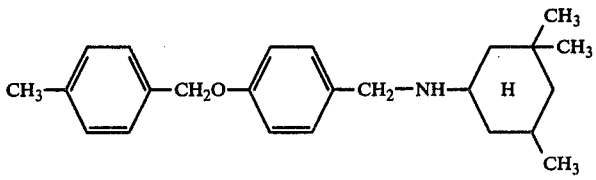 |
| 330. | 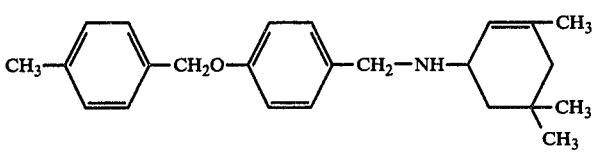 |
| 331. | 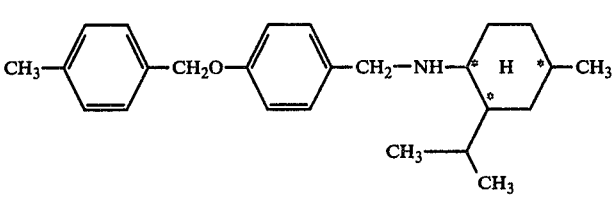 |
| 332. | 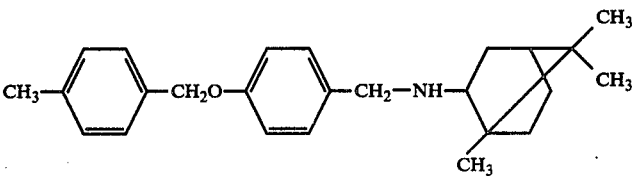 |
| 333. | 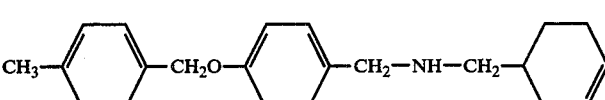 |
| 334. | 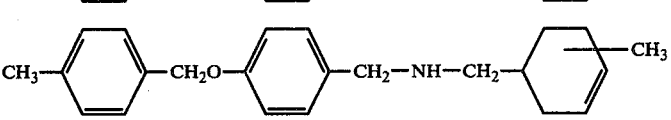 |
| 335. | 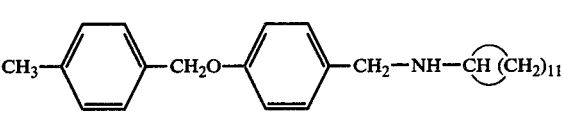 |
| 336. | 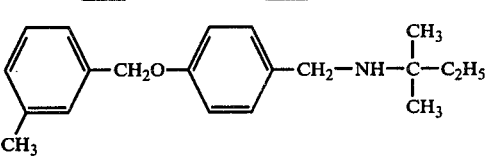 |
| 337. | 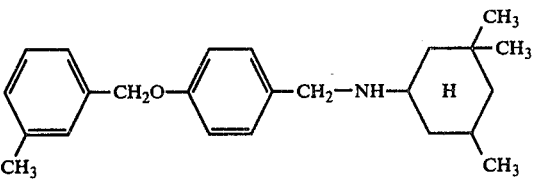 |
| 338. | 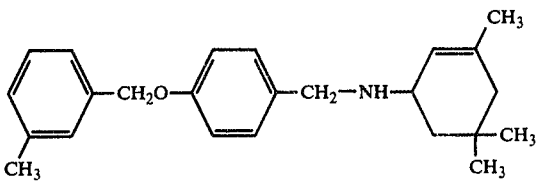 |

Table 2-continued
| Compound No. | |
|---|---|
| 339. | 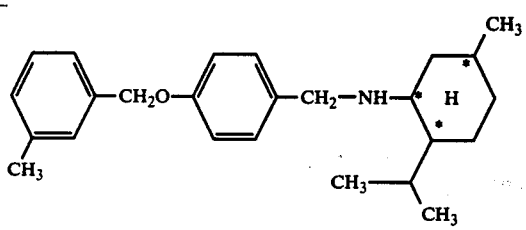 |
| 340. | 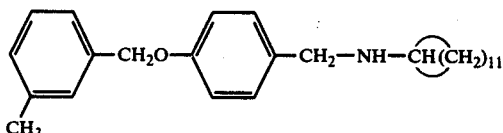 |
| 341. | 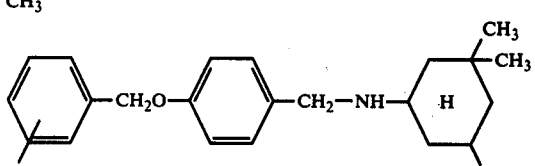 |
| 342. | 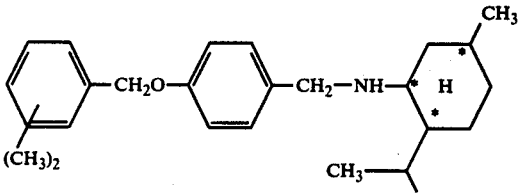 |
| 343. | 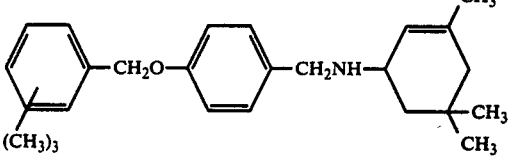 |
| 344. | 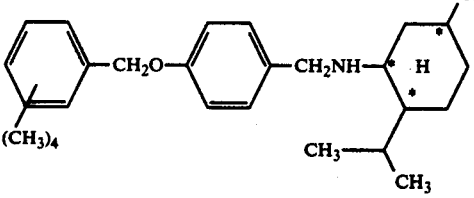 |
| 345. | 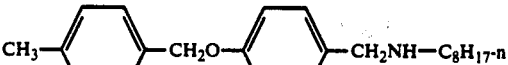 |
| 346. | 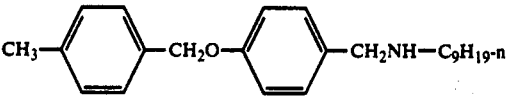 |
| 347. | 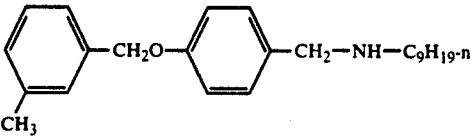 |
| 348. | 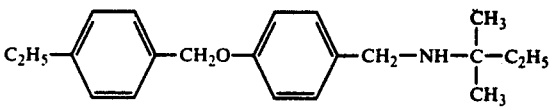 |
| 349. | 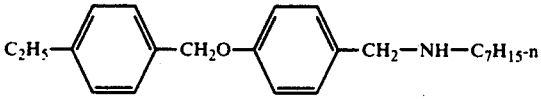 |

Table 2-continued
| Compound No. | |
|---|---|
| 350. | 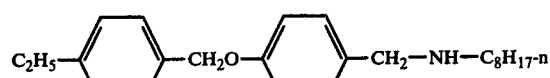 |
| 351. | 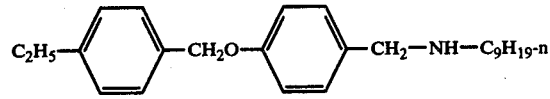 |
| 352. | 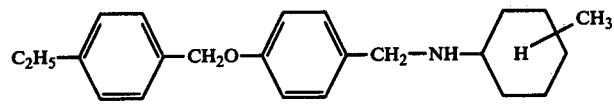 |
| 353. | 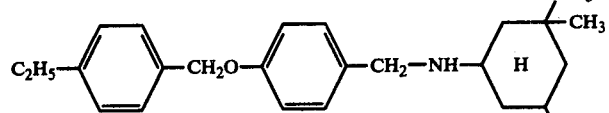 |
| 354. | 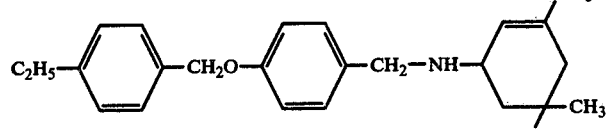 |
| 355. | 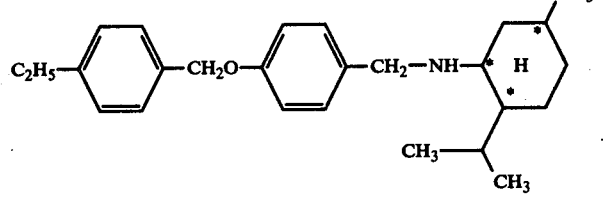 |
| 356. | 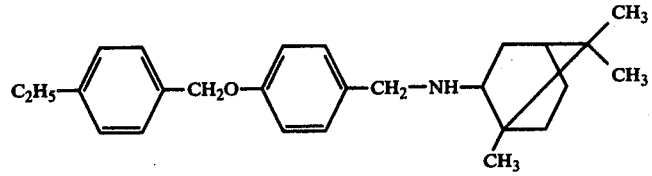 |
| 357. | 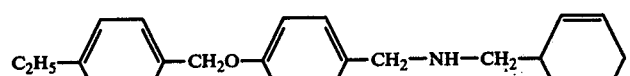 |
| 358. | 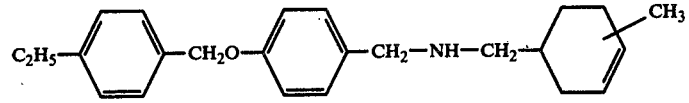 |
| 359. | 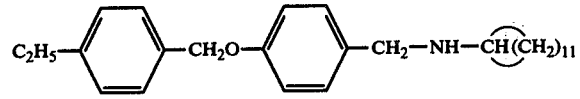 |
| 360. | 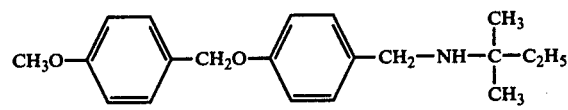 |
| 361. | 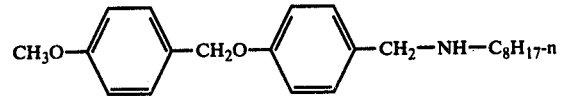 |
| 362. | 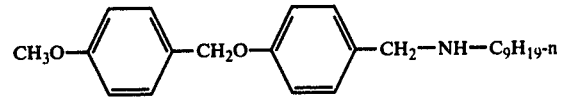 |

Table 2-continued
| Compound No. | |
|---|---|
| 363. | 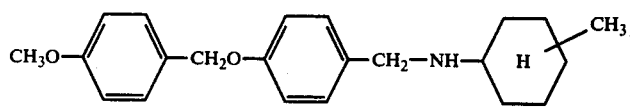 |
| 364. | 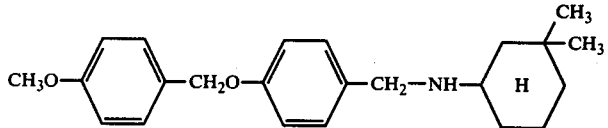 |
| 365. | 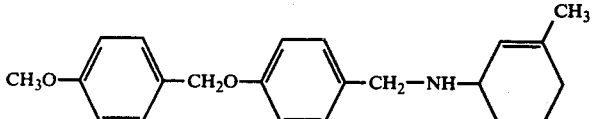 |
| 366. | 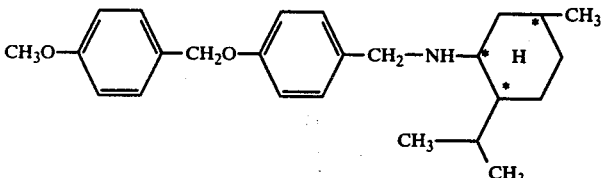 |
| 367. | 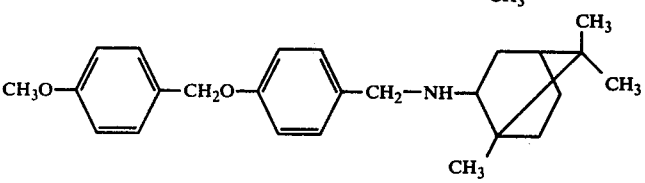 |
| 368. | 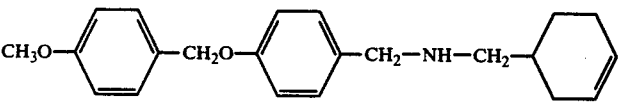 |
| 369. | 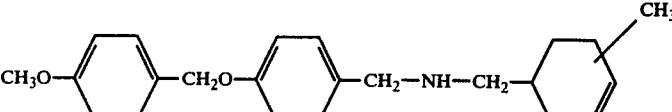 |
| 370. | 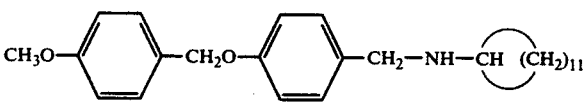 |
| 371. | 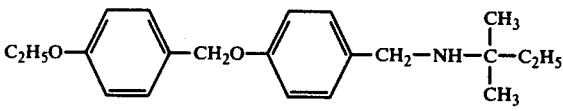 |
| 372. | 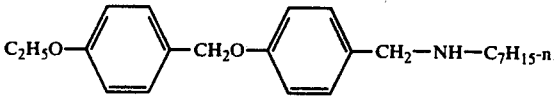 |
| 373. | 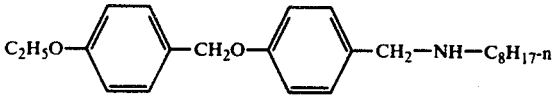 |
| 374. | 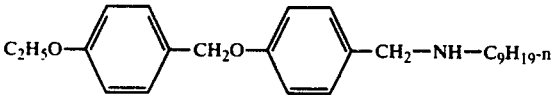 |
| 375. | 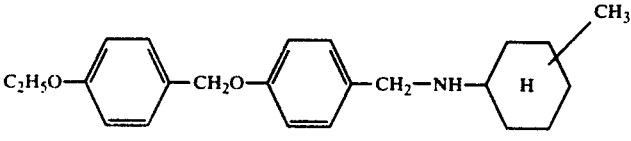 |

Table 2-continued
| Compound No. | |
|---|---|
| 376. | 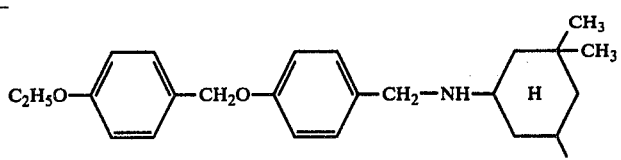 |
| 377. | 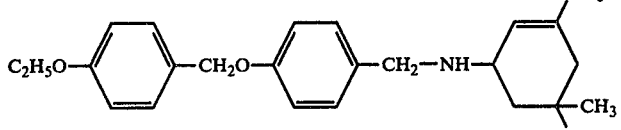 |
| 378. | 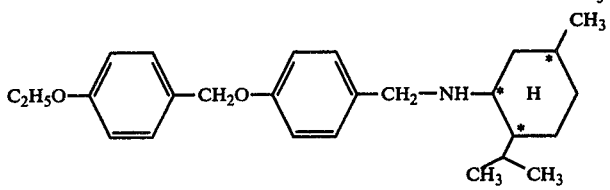 |
| 379. | 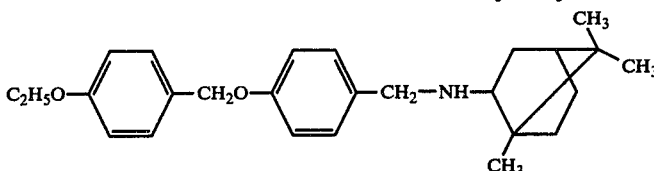 |
| 380. | 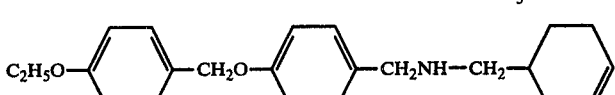 |
| 381. | 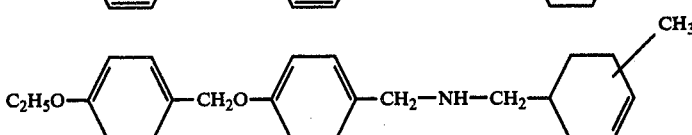 |
| 382. | 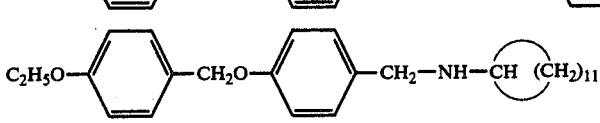 |
| 383. | 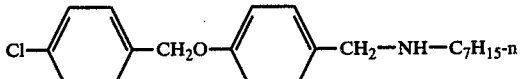 |
| 384. | 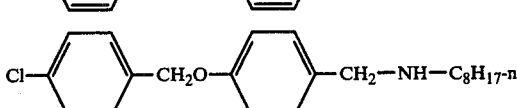 |
| 385. | 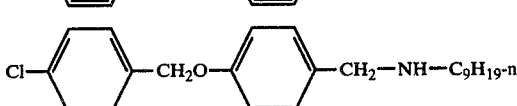 |
| 386. | 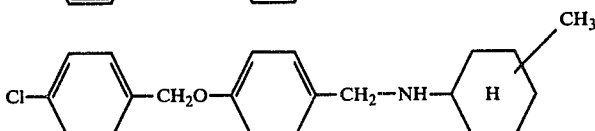 |
| 387. | 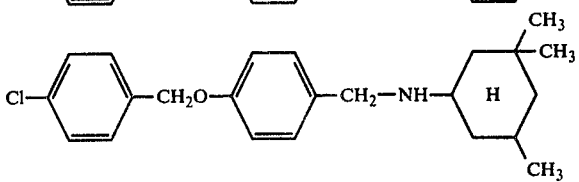 |

Table 2-continued
| Compound No. | |
|---|---|
| 388. | 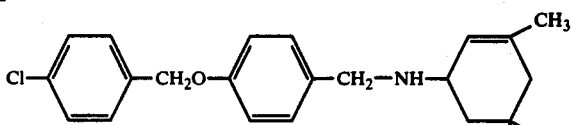 |
| 389. | 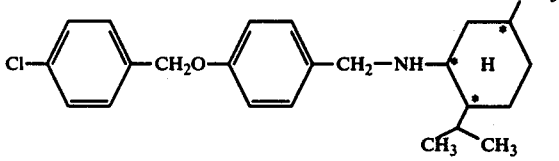 |
| 390. | 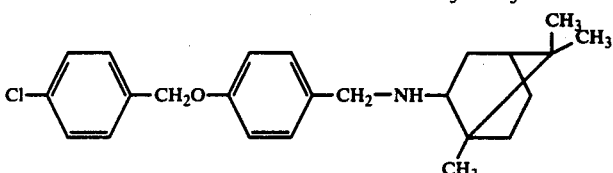 |
| 391. | 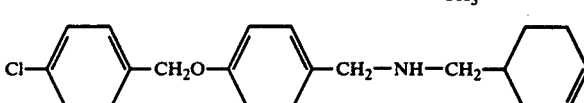 |
| 392. | 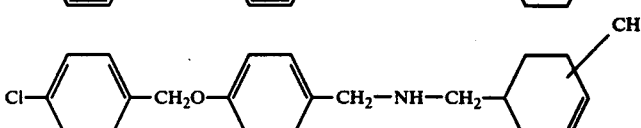 |
| 393. | 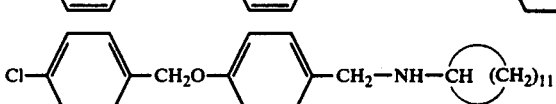 |
| 394. | 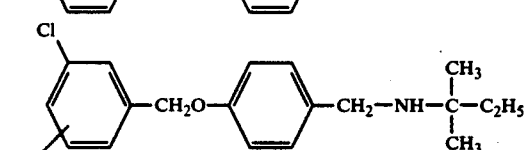 |
| 395. | 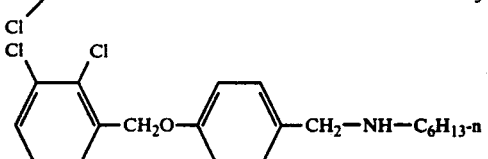 |
| 396. | 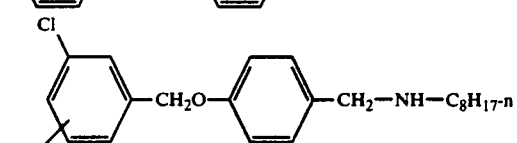 |
| 397. | 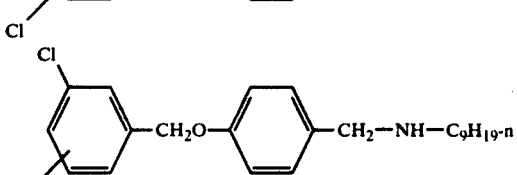 |
| 398. | 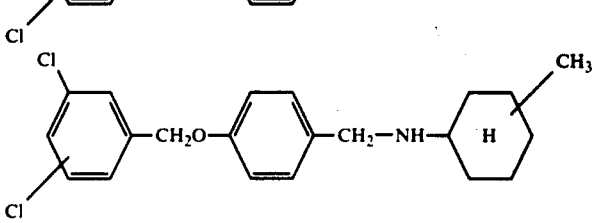 |

Table 2-continued
| Compound No. | |
|---|---|
| 399. | 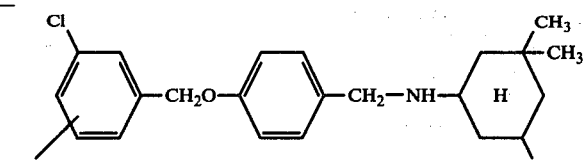 |
| 400. | 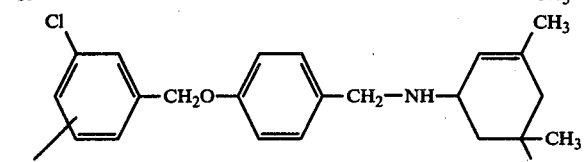 |
| 401. | 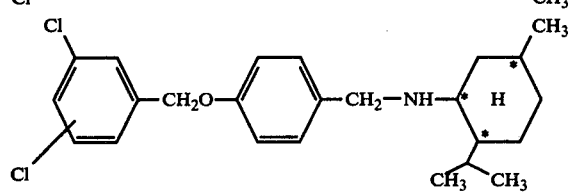 |
| 402. | 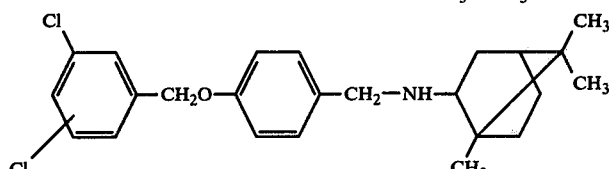 |
| 403. | 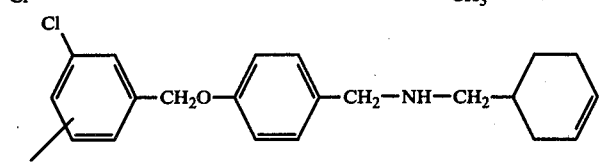 |
| 404. | 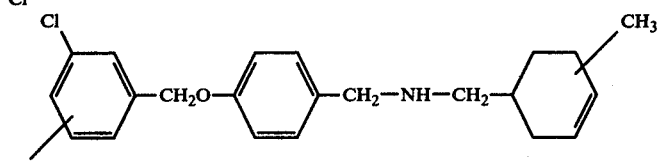 |
| 405. | 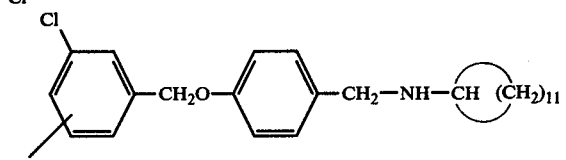 |
| 406. | 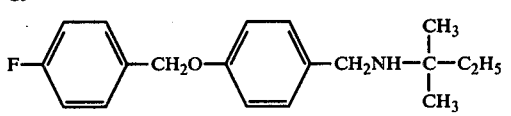 |
| 407. | 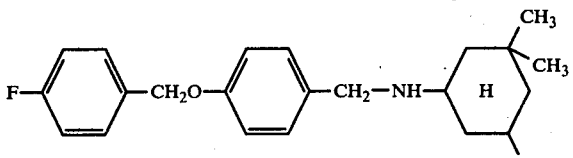 |
| 408. | 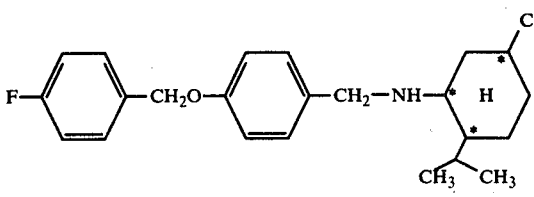 |

Table 2-continued

| Compound No. | Structure |
|---|---|
| 409. | 3-F-C6H4-CH2O-C6H4-CH2-NH-C(CH3)2-C2H5 |
| 410. | 3-F-C6H4-CH2O-C6H4-CH2-NH-(3,5,5-trimethylcyclohex-2-enyl) |
| 411. | 3-F-C6H4-CH2O-C6H4-CH2-NH-(2-isopropyl-5-methylcyclohexyl) (menthyl, stereocenters marked *) |
| 412. | C6H5-CH2O-C6H4-CH2-NH-(3,3,5-trimethylcyclohexyl) |
| 413. | C6H5-CH2O-C6H4-CH2-NH-(2-isopropyl-5-methylcyclohexyl) (menthyl, stereocenters marked *) |
| 414. | C6H5-CH2O-C6H4-CH2-NH-(2,6,6-trimethylbicyclo[3.1.1] pinanyl) |
| 415. | C6H5-CH2O-C6H4-CH2-NH-CH-(CH2)11 (cyclododecyl) |
| 416. | 4-CF3-C6H4-CH2O-C6H4-CH2-NH-C(CH3)2-C2H5 |
| 417. | 4-CF3-C6H4-CH2O-C6H4-CH2-NH-C9H19-n |
| 418. | 4-CF3-C6H4-CH2O-C6H4-CH2-NH-(4-methylcyclohexyl) |
| 419. | 4-CF3-C6H4-CH2O-C6H4-CH2-NH-(3,3,5-trimethylcyclohexyl) |

Table 2-continued
| Compound No. | |
|---|---|
| 420. | 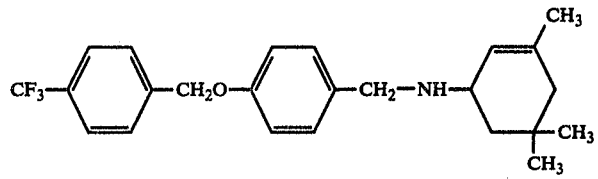 |
| 421. | 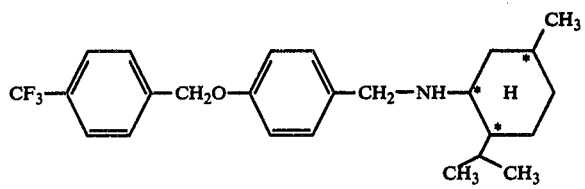 |
| 422. | 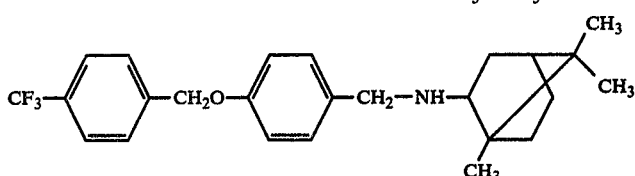 |
| 423. | 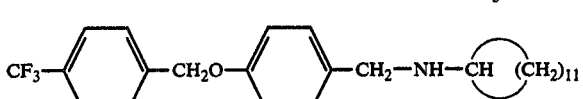 |
| 424. | 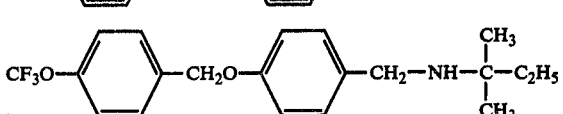 |
| 425. | 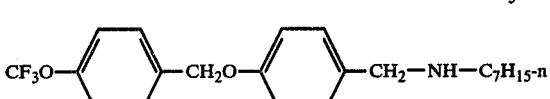 |
| 426. | 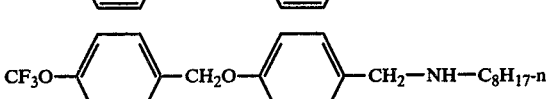 |
| 427. | 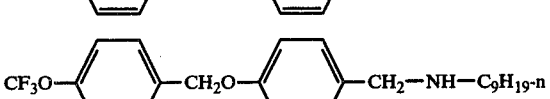 |
| 428. | 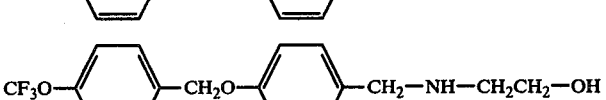 |
| 429. | 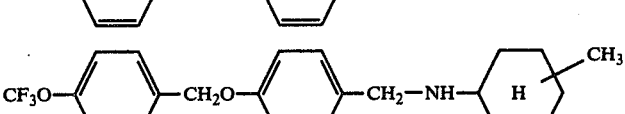 |
| 430. | 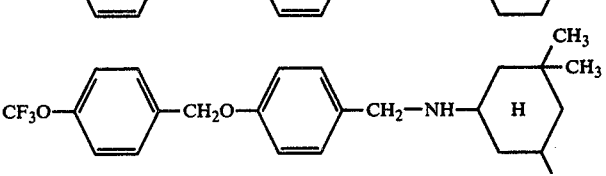 |
| 431. | 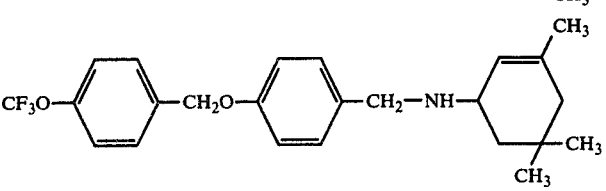 |

Table 2-continued
| Compound No. | |
|---|---|
| 432. | 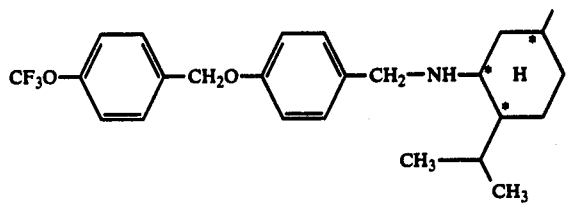 |
| 433. | 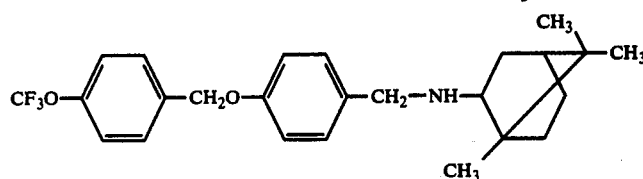 |
| 434. | 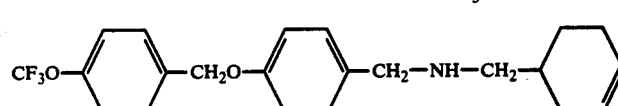 |
| 435. | 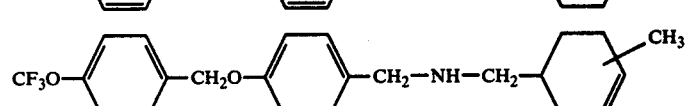 |
| 436. | 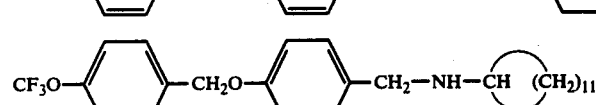 |
| 437. | 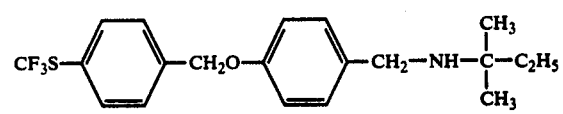 |
| 438. | 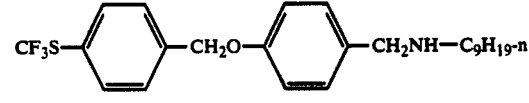 |
| 439. | 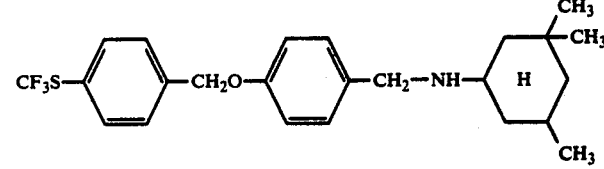 |
| 440. | 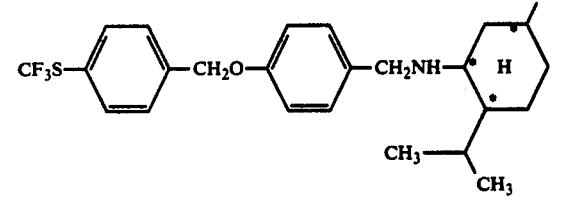 |
| 441. | 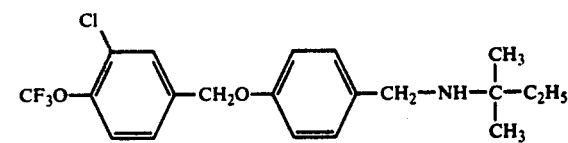 |
| 442. | 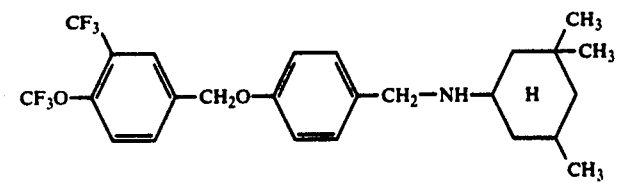 |

Table 2-continued

| Compound No. | Structure |
|---|---|
| 443. | 4-Cl-3-CF$_3$-C$_6$H$_3$-CH$_2$O-C$_6$H$_4$-CH$_2$NH-C$_9$H$_{19}$-n |
| 444. | 4-Cl-3-CF$_3$-C$_6$H$_3$-CH$_2$O-C$_6$H$_4$-CH$_2$-NH-(3,3,5-trimethylcyclohexyl) |
| 445. | 4-Cl-3-CF$_3$-C$_6$H$_3$-CH$_2$O-C$_6$H$_4$-CH$_2$-NH-(3,3,5-trimethylcyclohex-5-en-1-yl) |
| 446. | 4-Cl-3-CF$_3$-C$_6$H$_3$-CH$_2$O-C$_6$H$_4$-CH$_2$-NH-(2,6,6-trimethylbicyclo[3.1.1]heptyl) |
| 447. | C$_6$H$_5$-CH$_2$O-(3-OCH$_3$-C$_6$H$_3$)-CH$_2$-NH-C(CH$_3$)$_2$-C$_2$H$_5$ |
| 448. | C$_6$H$_5$-CH$_2$O-(3-OCH$_3$-C$_6$H$_3$)-CH$_2$-NH-C$_7$H$_{15}$-n |
| 449. | C$_6$H$_5$-CH$_2$O-(3,5-di-OCH$_3$-C$_6$H$_2$)-CH$_2$-NH-C$_8$H$_{17}$-n |
| 450. | C$_6$H$_5$-CH$_2$O-(3,5-di-OCH$_3$-C$_6$H$_2$)-CH$_2$-NH-C$_9$H$_{19}$-n |
| 451. | C$_6$H$_5$-CH$_2$O-(3,5-di-OCH$_3$-C$_6$H$_2$)-CH$_2$-NH-(4-methylcyclohexyl) |
| 452. | C$_6$H$_5$-CH$_2$O-(3,5-di-OCH$_3$-C$_6$H$_2$)-CH$_2$-NH-(3,3,5-trimethylcyclohexyl) |
| 453. | C$_6$H$_5$-CH$_2$O-(3,5-di-OCH$_3$-C$_6$H$_2$)-CH$_2$-NH-(3,3,5-trimethylcyclohex-5-en-1-yl) |

Table 2-continued
| Compound No. | |
|---|---|
| 454. | 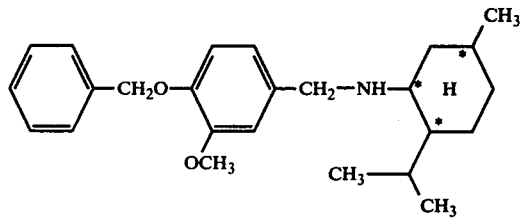 |
| 455. | 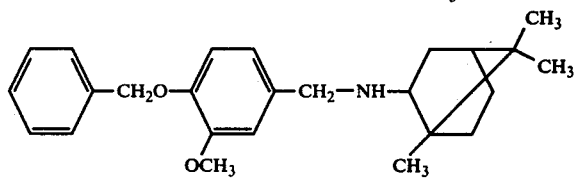 |
| 456. | 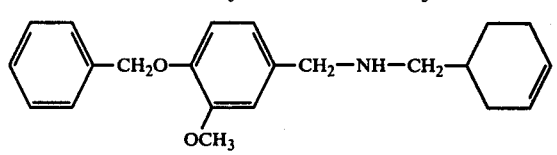 |
| 457. | 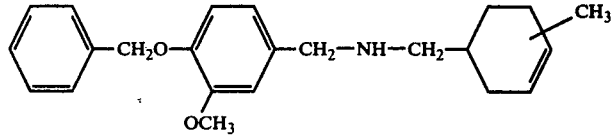 |
| 458. | 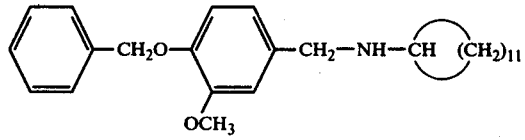 |
| 459. | 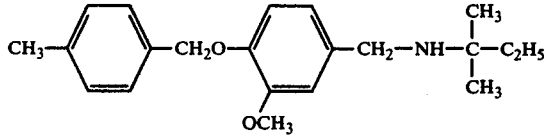 |
| 460. | 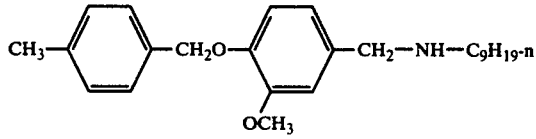 |
| 461. | 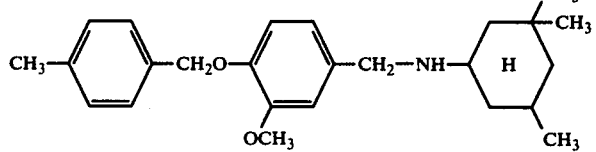 |
| 462. | 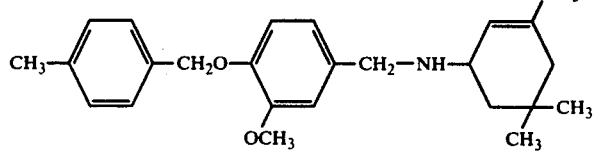 |
| 463. | 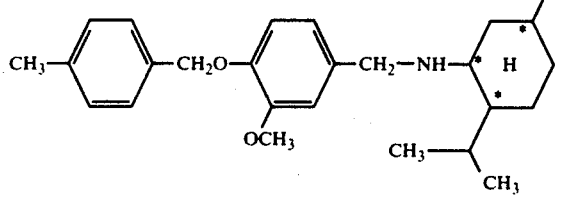 |

Table 2-continued

| Compound No. | |
|---|---|
| 464. | 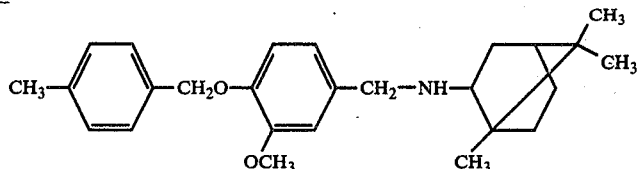 |
| 465. | 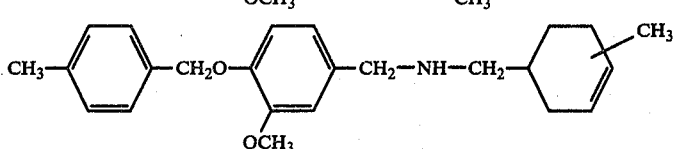 |
| 466. | 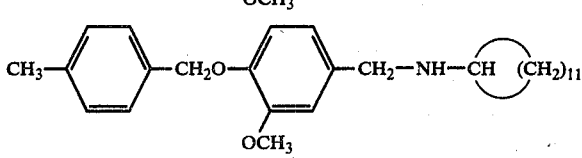 |

It will be appreciated that the instant specification and examples are set forth by way of illustration and not limitation, and that various modifications and changes may be made without departing from the spirit and scope of the present invention.

What is claimed is:

1. A substituted benzyl phenyl ether of the formula

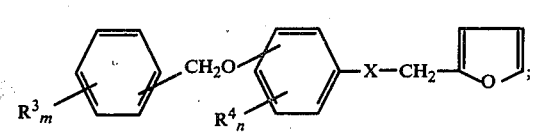

in which
X is

$R^1$ is H or methyl,
$R^3$ each independently is H, alkyl with 1–4 carbon atoms, alkoxy with 1–4 carbon atoms, halogen, trifluoromethyl, trichloromethyl, trifluoromethoxy, trifluoromethylmercapto or nitro,
$R^4$ each independently is H, halogen or alkoxy with 1 to 4 carbon atoms,
m is an integer from 1 to 5, and
n is an integer from 1 to 4,
or an acid addition salt thereof.

2. A compound according to claim 1, wherein X is

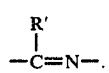

3. A compound according to claim 1, wherein X is

4. A compound according to claim 1, of the formula

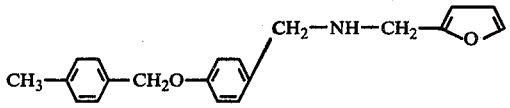

or an acid addition salt thereof.

5. A compound according to claim 1, of the formula

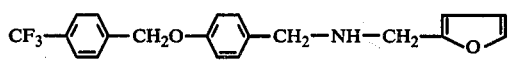

or an acid addition salt thereof.

6. An athropodicidal, nematicidal, fungicidal or bactericidal composition containing as active ingredient an arthropodicidally, nematicidally, fungicidally or bactericidally effective amount of a substituted benzyl phenyl ether according to claim 1 or an acid addition salt thereof in admixture with a diluent.

7. A method of combatting arthropods, nematodes, fungi or bacteria, which comprises applying to the arthropods, nematodes, fungi or bacteria, or to a habitat thereof, an arthropodicidally, nematicidally, fungicidally or bactericidally effective amount of a substituted benzyl phenyl ether according to claim 1 or an acid addition salt thereof.

8. The method according to claim 7 in which said substituted benzyl phenyl ether is

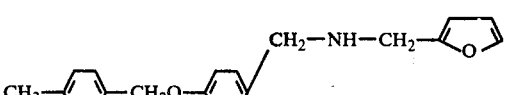

or an acid addition salt thereof.

* * * * *